United States Patent [19]

Royer et al.

[11] Patent Number: 5,449,602

[45] Date of Patent: Sep. 12, 1995

[54] TEMPLATE-DIRECTED PHOTOLIGATION

[75] Inventors: Garfield P. Royer, Elburn; Larry E. Morrison, Glen Ellyn; Kenneth A. Cruickshank, Naperville, all of Ill.

[73] Assignee: Amoco Corporation, Chicago, Ill.

[21] Appl. No.: 143,586

[22] Filed: Jan. 13, 1988

[51] Int. Cl.$^6$ .............. C12Q 1/68; C07H 15/12; C07H 17/00; C12N 15/00

[52] U.S. Cl. .............. 435/6; 536/24.3; 935/77; 935/78

[58] Field of Search .............. 435/6; 536/27; 935/77, 935/78

[56] References Cited

U.S. PATENT DOCUMENTS 4,542,102  9/1985  Dattagupta et al. .............. 435/6

FOREIGN PATENT DOCUMENTS 0185499  6/1986  European Pat. Off. .
0246864  11/1987  European Pat. Off. .

OTHER PUBLICATIONS

Heller et al., "Homogeneous Nucleic Acid Hybridization Diagnostics by Nonradiative Energy Transfer" in Chemical Abstracts, vol. 98, 1983, Abstract 212563j.

The Condensed Chemical Dictionary, Van Nostrand Reinhold Co (1971) p. 516.

Primary Examiner—Amelia Burgess Yarbrough
Assistant Examiner—Mindy B. Fleisher
Attorney, Agent, or Firm—Amoco Corporation

[57] ABSTRACT

Methods, apparatus and compositions are presented for ligating ligands together which bind to a common target. One embodiment includes polynucleotide probes having photoreactive functional groups. The probes are capable of assuming substantially contiguous reactive positions on a target polynucleotide placing the photoreactive groups in juxtaposition. Activation of the photoreactive functional groups with radiant energy form a probe reaction product in which the probes are bound to each other.

15 Claims, 1 Drawing Sheet

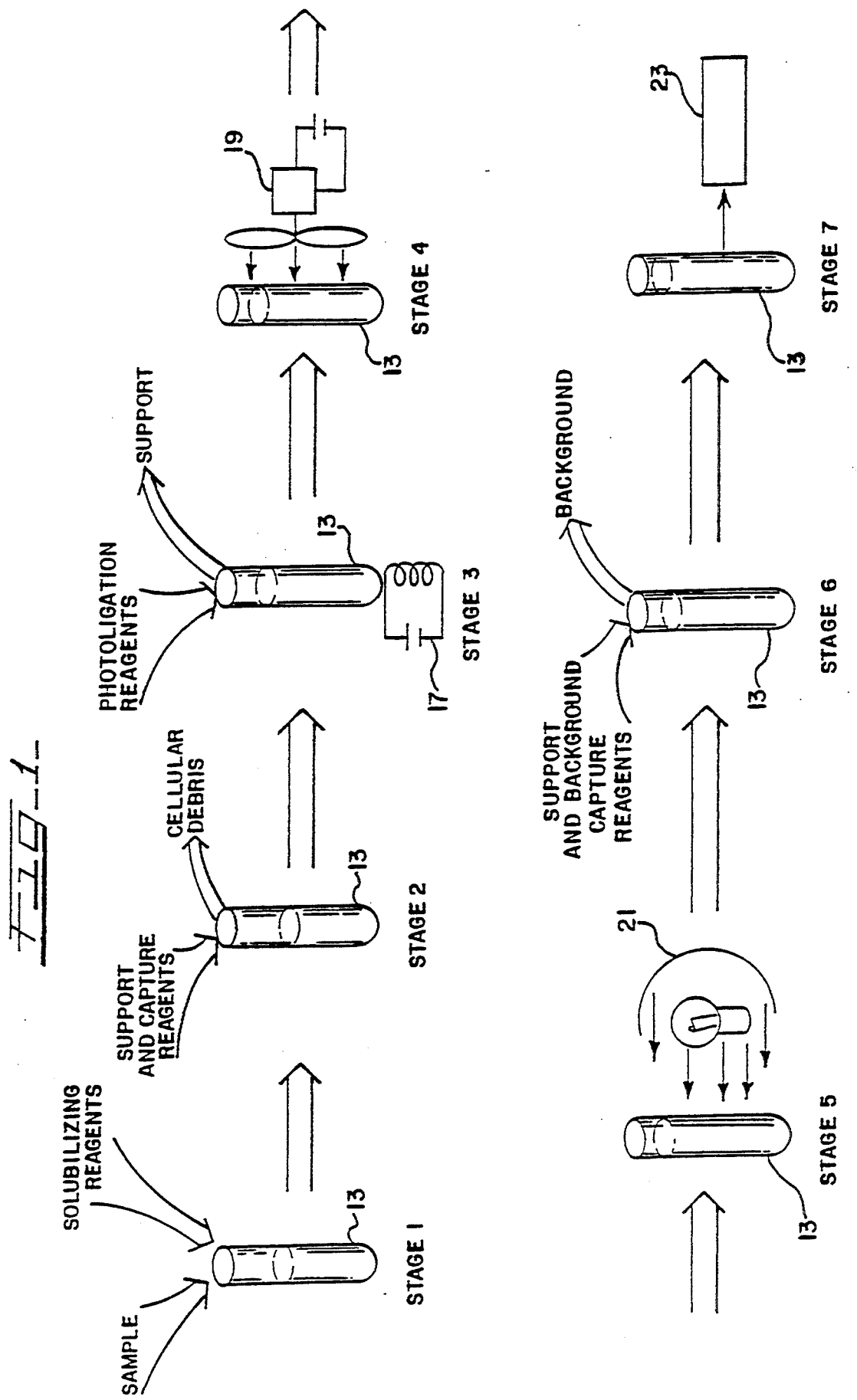

TEMPLATE-DIRECTED PHOTOLIGATION

BACKGROUND OF THE INVENTION

The present invention pertains to methods, reagents, compositions, kits, and apparatus for use in ligating substantially contiguous ligands together on a target template. In particular, the present invention relates to methods, reagents, compositions, and kits for performing deoxyribonucleic acid (DNA) or ribonucleic acid (RNA) hybridization assays.

The following definitions are provided to facilitate an understanding of the present invention.

The term "target" or "target molecule" refers to a molecule of interest, i.e. the molecule whose presence one wishes to know. The target is a member of a biological binding pair.

The term "biological binding pair" as used in the present application refers to any pair of molecules which exhibit mutual affinity or binding capacity. For the purposes of the present application, the term "ligand" will refer to one molecule of the biological binding pair, and the term "antiligand" or "receptor" will refer to the opposite molecule of the biological binding pair. For example, without limitation, embodiments of the present invention have application in nucleic acid hybridization assays where the biological binding pair includes two complementary strands of nucleic acid. One of the strands is designated the ligand and the other strand is designated the antiligand or receptor. One of the strands may also be a target molecule. The designation of ligand or antiligand is a matter of arbitrary convenience. The biological binding pair may include antigens and antibodies, drugs and drug receptor sites, and enzymes and enzyme substrates, to name a few. A biological binding pair is capable of forming a complex under binding conditions.

The term "probe" refers to a ligand of known qualities capable of selectively binding to a target antiligand or receptor. As applied to nucleic acids, the term "probe" refers to a strand of nucleic acid having a base sequence complementary to a target strand. The probe and the target are capable of forming a probe target complex under binding conditions.

The term "label" refers to a molecular moiety capable of detection including, by way of example, without limitation, radioactive isotopes, enzymes, luminescent agents, precipitating agents, and dyes. The term "agent" is used in a broad sense, including any molecular moiety which participates in reactions which lead to a detectable response. The term "cofactor" is used broadly to include any molecular moiety which participates in reactions with the label.

The term "amplify" is used in the broad sense to mean creating an amplification product, which may include by way of example, additional target molecules, or target-like molecules, capable of functioning in a manner like the target molecule, or a molecule subject to detection steps in place of the target molecule, which molecules are created by virtue of the presence of the target molecule in the sample. In the situation where the target is a polynucleotide, additional target, or target-like molecules, or molecules subject to detection can be made enzymatically with DNA or RNA polymerases.

The term "reactive functional group" refers to a functional group capable of forming a covalent bond upon activation between two ligands held in a reactive position. Activation may include chemical or physical changes to the environment.

The term "photoreactive functional group" refers to a reactive functional group capable of forming a covalent bond upon photoactivation with radiant energy between two ligands held in a reactive position.

An example of a photoreactive functional group includes, without limitation, olefins, conjugated olefins, ketones, α, β-unsaturated ketones, azides, conjugated polyolefins characterized by conjugated double bonds and ketone functionality and aromatic compounds. Photoreactive functional groups can be further characterized as coumarins, psoralens, anthracenes, pyrenes, carotenes, tropones, chromones, quinones, maleic anhydride, alkyl maleimide and derivatives thereof. Further examples of photoreactive functional groups can be found in the reference J. G. Calvert, James N. Pitts, Jr., *Photochemistry*, pages 536–48, John Wiley Sons, Inc. (1966), incorporated by reference herein.

The term "contiguous" means an adjacent area of a molecule. By way of example, in the case of biological binding pairs, where a first ligand binds to a receptor target molecule, the area surrounding and adjacent to the first ligand is open and capable of binding to a second ligand contiguous to the first. In the context of polynucleotides, where a first probe binds to an area of a polynucleotide target molecule, an adjacent mutually exclusive area along the length of the target molecule can bind to a second probe which will then be contiguous to the first. The target molecule acts as a template, directing the position of the first probe and the second probe. The term "substantially contiguous" is used in the functional sense to include spatial orientations which may not touch, may not abut, or may overlap yet function to bring a reactive covalent functional group into a reactive position.

The term "capture ligand" means a ligand capable of specifically binding with a capture antiligand associated with a support.

The term "retrievable support" is used in a broad sense to describe an entity which can be substantially dispersed within a medium and removed or separated from the medium by immobilization, filtering, partitioning, or the like.

The term "support", when used alone, includes conventional supports such as filters and membranes as well as retrievable supports.

The term "reversible", in regard to the binding of ligands and antiligands, means capable of binding or releasing upon imposing changes which do not permanently alter the gross chemical nature of the ligand and antiligand. For example, without limitation, reversible binding would include such binding and release controlled by changes in pH, temperature, and ionic strength which do not destroy the ligand or antiligand.

Genetic information is stored in living cells in thread-like molecules of DNA. In vivo, the DNA molecule is a double helix, each strand of which is a chain of nucleotides. Each nucleotide is characterized by one of four bases: adenine (A), guanine (G), thymine (T), and cytosine (C). The bases are complementary in the sense that, due to the orientation of functional groups, certain base pairs attract and bond to each other through hydrogen bonding and π-stacking interactions. Adenine in one strand of DNA pairs with thymine in an opposing complementary strand. Guanine in one strand of DNA pairs with cytosine in an opposing complementary strand. In RNA, the thymine base is replaced by uracil (U) which pairs with adenine in an opposing complementary strand.

The genetic code of a living organism is carried upon the DNA strand in the sequence of base pairs. DNA consists of covalently linked chains of deoxyribonucleotides and RNA consists of covalently linked chains of ribonucleotides.

Each nucleic acid is linked by a phosphodiester bridge between the 5'-hydroxyl group of the sugar of one nucleotide and the 3'-hydroxyl group of the sugar of an adjacent nucleotide. Each linear strand of naturally occurring DNA or RNA has one terminal end having a free 5'-hydroxyl group and another terminal end having a 3'-hydroxyl group. The terminal ends of polynucleotides are often referred to as being 5'-termini or 3'-termini in reference to the respective free hydroxyl group. Naturally occurring polynucleotides may have a phosphate group at the 5'-terminus. Complementary strands of DNA and RNA form antiparallel complexes in which the 3'-terminal end of one strand is oriented and bound to the 5'-terminal end of the opposing strand.

Nucleic acid hybridization assays are based on the tendency of two nucleic acid strands to pair at their complementary regions. Presently, nucleic acid hybridization assays are primarily used to detect and identify unique DNA or RNA base sequences or specific genes in a complete DNA molecule, in mixtures of nucleic acid, or in mixtures of nucleic acid fragments.

The identification of unique DNA or RNA sequences or specific genes within the total DNA or RNA extracted from tissue or culture samples, may indicate the presence of physiological or pathological conditions. In particular, the identification of unique DNA or RNA sequences or specific genes, within the total DNA or RNA extracted from human or animal tissue, may indicate the presence of genetic diseases or conditions such as sickle cell anemia, tissue compatibility, cancer and precancerous states, or bacterial or viral infections. The identification of unique DNA or RNA sequences or specific genes within the total DNA or RNA extracted from bacterial cultures may indicate the presence of antibiotic resistance, toxicants, viral- or plasmid-born conditions, or provide identification between types of bacteria.

Thus, nucleic acid hybridization assays have great potential in the diagnosis and detection of disease. Further potential exists in agriculture and food processing where nucleic acid hybridization assays may be used to detect plant pathogenesis or toxicant-producing bacteria.

One of the most widely used polynucleotide hybridization assay procedures is known as the Southern blot filter hybridization method or simply, the Southern procedure (Southern, E., *J. Mol. Biol.*, 98, 503, 1975). The Southern procedure is used to identify target DNA or RNA sequences. The procedure is generally carried out by subjecting sample RNA or DNA isolated from an organism, potentially carrying the target sequence of interest, to restriction endonuclease digestion to form DNA fragments. The sample DNA fragments are then electrophoresed on a gel such as agarose or polyacrylamide to sort the sample fragments by length. Each group of fragments can be tested for the presence of the target sequence. The DNA is denatured inside the gel to enable transfer to nitrocellulose sheets. The gel containing the sample DNA fragments is placed in contact (blotted) with nitrocellulose filter sheets or diazotized paper to which the DNA fragments transfer and become bound or immobilized. The nitrocellulose sheet containing the sample DNA fragments is then heated to approximately 85° C. to immobilize the DNA. The nitrocellulose sheet is then treated with a solution containing a denatured (single-stranded) radio-labeled DNA probe. The radio-labeled probe includes a strand of DNA having a base sequence complementary to the target sequence and having a radioactive moiety which can be detected.

Hybridization between the probe and sample DNA fragments is allowed to take place. During the hybridization process, the immobilized sample DNA is allowed to recombine with the labeled DNA probe and again form double-stranded structures.

The hybridization process is very specific. The labeled probe will not combine with sample DNA if the two DNA entities do not share substantial complementary base pair organization. Hybridization can take from 3 to 48 hours, depending on given conditions.

Unhybridized DNA probe is subsequently washed away. The nitrocellulose sheet is then placed on a sheet of X-ray film and allowed to expose. The X-ray film is developed with the exposed areas of the film identifying DNA fragments which have hybridized to the DNA probe and therefore have the base pair sequence of interest.

The use of nucleic acid hybridization assays has been hampered in part due to the inability of investigators to detect a signal from a probe indicating the presence of target over background caused by nonspecific binding of the probe to non-target entities. The signal to noise ratio can be improved by decreasing background noise by segregating the nucleic acid from other cellular debris. Background noise is sometimes reduced by subjecting a sample, potentially containing the nucleic acid of interest, to which probe has been added, to stringent washes which will remove probe which is only nonspecifically bound. However, as a practical matter, a small amount of probe is disassociated from the target with each wash, particularly as stringency increases. Investigators must balance between limiting background noise and retaining enough signal to detect target.

The signal to noise ratio may also be improved by increasing or amplifying the signal which can be generated from a single target molecule. As a practical matter, background noise is usually amplified to some degree with the signal. Investigators must balance between amplifying signal and maintaining background noise to a level at which the target can be detected.

The techniques used to improve signal-to-noise ratios in nucleic acid assay systems must be compatible with the overall environment in which the system is to be used. For research purposes, time may be of less importance than maximizing a signal-to-noise ratio. However, in medical applications and in food testing, time may be a critical factor. For example, time considerations, in part, are driving immuno and nucleic acid diagnostics away from radioactive labels to nonisotopic systems. Nonisotopic systems do not require long development times necessary for X-ray film. Time considerations are also driving medical and food diagnostics away from culture techniques to other systems of detection.

The problem of developing a useful and reliable signal-to-noise ratio has led researchers to several techniques. Yabusaki et al. in PCT Patent Application PCT/US84/02024, International Publication Number WO85/02628 entitled *Nucleic Acid Hybridization Assay* report the use of photoreactive crosslinking reactions to link a probe to target DNA. However, the Yabusaki reference does not suggest means for amplifying the signal or photoreactively forming covalent bonds between contiguous ligands on a target template. European Patent Application 85308910.0 to Hunkapiller et al. entitled *Detection of Specific Sequences in Nucleic Acids* suggests that two contiguous probes can be ligated together enzymatically to form a detectable unit. However, enzyme ligations are inefficient, particularly, at low target concentrations normally encountered in analytical applications, and enzymatic ligation is time-consuming. Enzymatic ligation requires many complex steps and is subject to variations in enzyme activity. Enzymes require two hours or more for proper incubation. Two hours of incubation added to other assay steps, including sample preparation, hybridization, and detection, enlarges the total duration of the assay system limiting its use in many clinical settings.

SUMMARY OF THE INVENTION

The present invention features methods, reagents, compositions, kits and apparatus for ligating substantially contiguous ligands to each other on a target template. Embodiments of the present invention are well-suited for performing assays for target polynucleotide strands of interest. Further embodiments are well-suited for template-directed assembly of large molecules.

Briefly, an embodiment of the present invention includes a method for ligating substantially contiguous ligands which bind to a common target. The method includes contacting a target with a first ligand and a second ligand. At least one of the first and second ligands has a reactive functional group capable of forming a covalent bond, between the first ligand and the second ligand, upon activation, when the first and second ligands are placed in a reactive position. The first ligand and the second ligand are both capable of simultaneously binding to the target in a reactive position to form a receptor first-second ligand complex. Next, the method includes the step of activating the reactive functional group to form a covalent bond between the first and second ligands creating a ligand reaction product.

Preferred embodiments of the present invention include photoreactive functional groups. The photoreactive functional group is activated by radiant energy.

Embodiments of the present method can be used to assemble large molecules from individual segments. For example, without limitation, embodiments of the present invention have applications in the assembly of large DNA or RNA molecules.

Embodiments of the present invention also have particular application in diagnostics to detect the presence of a target molecule in a sample.

In one embodiment, after activating the reactive functional group, the sample is monitored for the presence of the ligand reaction product which is indicative of the presence of target.

A preferred embodiment includes a first ligand and a second ligand having at least one photoreactive functional group. The first ligand and the second ligand are brought together upon a target molecule. The photoreactive functional group is activated with radiant energy to form a ligand-ligand reaction product having detectable properties which are distinct from either ligand separately. The detection of the ligand-ligand reaction product is indicative of the presence of the target receptor molecule.

Embodiments of the present invention are suitable for assay systems to detect polynucleotide target molecules. Thus, a further embodiment of the present method includes an assay method wherein the first probe and the second probe are polynucleotide strands. At least one probe has a photoreactive group capable of binding the first and second probe together to form a probe reaction product when the photoreactive functional group is activated and when the first and second probes are in a reactive position. The first probe and the second probe are capable of assuming the reactive position upon binding to substantially contiguous portions of a target polynucleotide. The photoreactive functional group is activated to form a probe reaction product having detectable properties distinct from either probe separately. The detection of the probe reaction product is indicative of the presence of the target molecule.

In the case where samples of clinical, agricultural or industrial origin are examined, preferred embodiments will include sample processing steps to capture and segregate the target from extraneous debris, steps to reduce background and steps to amplify the target.

A preferred method for assaying a sample for a target polynucleotide includes contacting a sample under binding conditions with a first probe, a second probe, and a support. The first probe and the second probe have at least one photoreactive functional group capable of binding the first probe and the second probe together to form a probe reaction product in the presence of radiant energy when the first and the second probe are placed in a reactive position. The first and second probe are capable of binding to the target polynucleotide to form a target first-second probe complex wherein the first and the second probe are in the reactive position. At least one of the probes includes a capture ligand. The support includes a capture antiligand to allow association of the probe with a support. The second probe includes a label moiety capable of detection. Following contacting the sample with the first probe and the second probe, the method includes the step of activating the functional group to form a probe reaction product. The method includes the step of forming a probe reaction product-support complex with or without association with target. In the situation where the capture association is reversible, the probe reaction product and/or target are released into a new media apart from cellular debris and non-target polynucleotides released during sample processing. Where the capture ligand-antiligand association is irreversible, the support can be subjected to stringent washes and purges to remove cellular debris and non-target polynucleotides. The probe reaction product is available for further processing including amplification and detection steps.

In one embodiment of the present invention, the first probe or the probe reaction product is irreversibly associated with the capture support by further photoreactive functional groups. Preferably, the support is retrievable, capable of substantially homogeneous dispersion into the medium containing the probe with the capture ligand.

In the situation where the second probe, having a label moiety, includes a second capture ligand, which ligand is substantially impaired when the second probe is bound to target or part of a probe reaction product, a second support having a second capture antiligand is used to capture second probe which is unbound to target or not a part of a probe reaction product. Capture of the second probe apart from the target or probe reaction product reduces background noise.

Preferably, the first probe and the second probe both include photoreactive functional groups capable of interacting upon activation with radiant energy to produce a probe reaction product.

Preferably, one photoreactive functional group is positioned at or about the 3' end of one polynucleotide probe in order to interact with a second photoreactive functional group at or about the 5' end of a second probe. Thus, a first probe and a second probe will assume a reactive orientation upon a polynucleotide target molecule with the 3' terminus of one probe bearing a photoreactive functional group substantially contiguous and proximal to the 5' terminus of a second probe bearing a second photoreactive functional group.

Preferably, the wavelength is selected to activate the photoreactive functional group, to minimize DNA photochemistry, and to minimize disruption of the probe reaction product, if formed. For coumarin-like photoreactive functional groups a wavelength of between approximately 300 nanometers and 380 nanometers inclusive is preferred. Further, a preferred photoreactive functional group has an extinction coefficient greater than 1,000 mole $^{-1} \cdot l \cdot cm^{-1}$ to permit excitation to reactive energy levels, and, most preferably, an extinction coefficient of of approximately 10,000 mole $^{-1} \cdot l \cdot cm^{-1}$.

Preferred photoreactive functional groups include benzo-alpha-pyrones (trivial name coumarins). The structural formula for benzo-alpha-pyrone, coumarin, is set forth below:

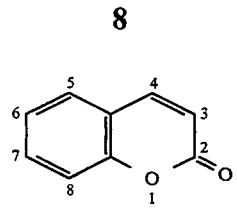

Preferably, the coumarin derivative includes a hydroxy or methoxy group at positions 5 or 7 in conjunction with the alpha-beta unsaturated lactone functionality to give a 5-hydroxy-coumarin or a 7-methoxy-coumarin having a significant absorbance at about 320 nanometers. Further, substituent grouping on the benzene ring allows attachment of the coumarin derivative to amino functionalized DNA. Thus, 5-hydroxy-coumarin and 7-hydroxy-coumarin are derivatized by termination of the linking oxymethylene chain with a N-hydroxysuccinimide ester grouping which is known to react with aliphatic amino groups in aqueous solution. Preferably, the coumarin methylene chain includes from between 1 to 10 atoms inclusive; and, most preferably, the methylene chain is 3 atoms in length. The methylene chain may include atoms and functionality other than carbon including, by way of example, oxygen and nitrogen.

Preferably, the functionalized DNA includes a methylene chain. The DNA methylene chain includes functionality to react with the coumarin methylene chain. A preferred functionality on the DNA methylene chain is an amine. The DNA methylene chain is preferably from between 1 to 10 atoms in length inclusive and most preferably 4 atoms in length where the terminal atom is an amine. The DNA methylene chain may include atoms and functionality other than carbon including, by way of example, oxygen and nitrogen.

The DNA and coumarin methylene chains form a DNA-coumarin linkage. The linkage allows the coumarin derivatives sufficient freedom of motion to orientate properly for a 2 plus 2 cyclo addition reaction as set forth below:

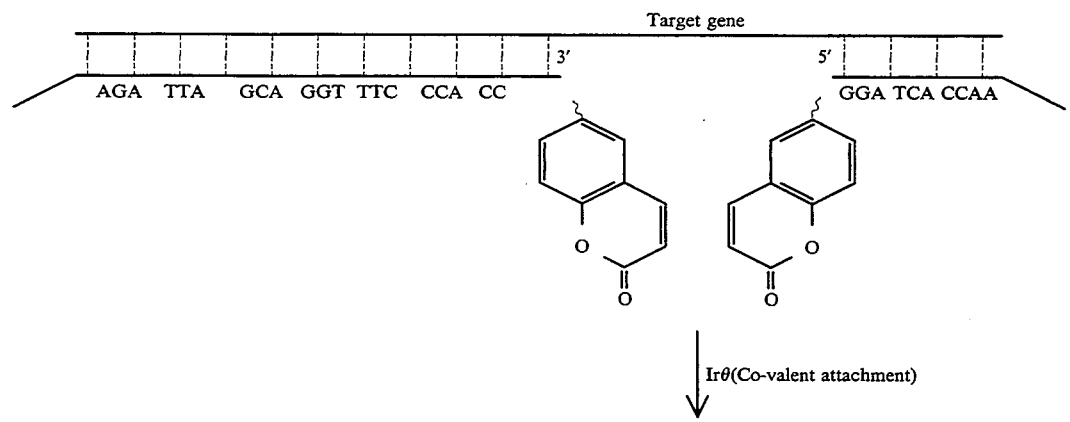

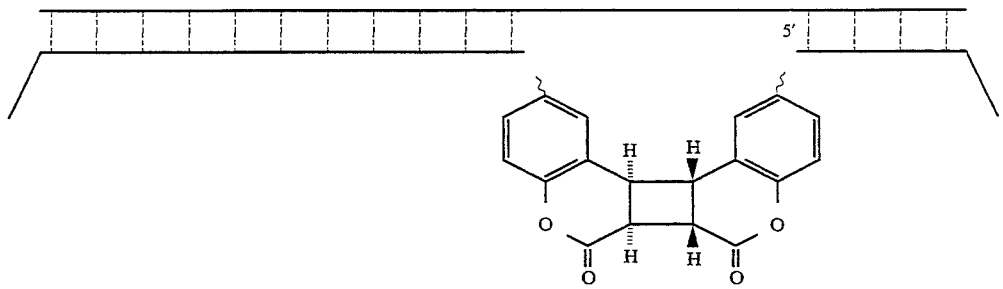

Preferably, the linkage is from between 1 to 10 atoms in length. A preferred coumarin derivative is described below:

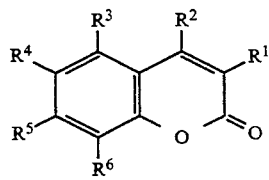

Preferably, R groups 1 through 6 are selected from the group consisting of —H, —CH$_3$, —CH$_2$Cl, —CH$_2$Br, —CH$_2$I, —CH$_2$F, —CHCl$_2$, —CHBr$_2$, —CHI$_2$, —CHF$_2$, —CH$_2$OH, —CH$_2$OCH$_3$, —CH$_2$NH$_2$, —N$_3$, —COOH, —COOCH$_3$, —COOCH$_2$CH$_3$, —NH$_2$, —NO$_2$, —CBr$_3$, —CI$_3$, —CF$_3$, —CCl$_3$, —CH(CH$_3$)$_2$, —C(CH$_3$)$_3$, —Cl, —Br, —I, —F, and —O(CH$_2$)$_n$CH$_3$(n=0 to 10) wherein, one of the R groups includes a reactive moiety for linking to a functionalized DNA molecule. Preferably, the DNA molecule is functionalized with an amine group.

Preferably, the photoreactive functional group will be covalently bound to the probe molecule via a chemical reaction such as alkylation, condensation or addition.

A further group of compounds suitable as photoreactive functional groups include psoralens having the general formula set forth below:

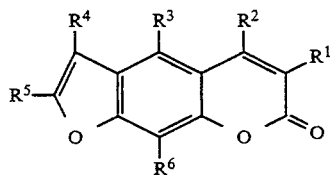

As set forth above, R$_1$ through R$_6$ respectively are selected from the group consisting of for example, —H, —CH$_3$, —CH$_2$Cl, —CH$_2$Br, —CH$_2$I, —CHCl$_2$, —CH$_2$F, —CHBr$_2$, —CHI$_2$, —CHF$_2$, —CH$_2$OH, —CH$_2$NH$_2$, —N$_3$, —COOH, —COOCH$_3$, —COOCH$_2$CH$_3$, —NH$_2$, —NO$_2$, —CI$_3$, —CBr$_3$, —CF$_3$, —CCl$_3$, —CH(CH$_3$)$_2$, —C(CH$_3$)$_3$, —Cl, —Br, —I, —F, and —O(CH$_2$)$_n$CH$_3$(n=0 to 10) wherein, one of the R groups includes a reactive moiety for linking to a functionalized DNA molecule. Preferably, the DNA molecule is functionalized with an amine group.

Further functional groups exhibiting photoreactive characteristics include olefins, conjugated olefins, ketones, α, β-unsaturated ketones, azides, conjugated polyolefins characterized by conjugated double bonds and ketone functionality, maleic anyhdride, alkyl maleimide, tropones, chromones, quinones and the like.

Embodiments of the present invention feature methods for amplifying a signal produced by hybridizing a probe to a target molecule. The present method produces a memory of the hybridization process by covalently linking two probes in a substantially irreversible manner to form a probe reaction product. Following covalent linking, the probe reaction product can be removed from the target molecule allowing a different first and second probe molecule to hybridize and assume a reactive position upon the same target molecule. The new first and second probe molecules are photoligated to record a further hybridization from the same target. The cycling of unreacted probe molecules with the target molecule and the formation of photoligated probe reaction product may continue as needed limited only by the efficiency of the photoligation process to produce an ever-increasing signal based on the presence of a target molecule.

Thus, one embodiment of the present invention includes a method to increase the signal produced from a single target molecule. The method includes the steps of imposing binding conditions on a sample potentially containing a target molecule of interest in the presence of excess probe reagent containing a first probe and a second probe. The first probe and second probe include at least one photoreactive functional group capable of binding the first probe to the second probe when the photoreactive functional group is activated and the probes are in a reactive position. A further step includes activating the photoreactive functional group means with radiant energy to form a detectable probe reaction product. A further step includes allowing the probe reaction product to disassociate from the target molecule to permit a further first probe and a further second probe to assume the position of the probe reaction product on the target molecule. A further step includes activating the photoreactive functional group to produce a plurality of probe reaction products from a single target molecule, thus creating additional signals. The cycle can be repeated as desired limited by the efficiency of the photoreaction.

In the situation where the target molecule is a polynucleotide, binding and releasing conditions are generally imposed respectively by adjusting pH, ionic strength or temperature. All of the above adjustments are time-consuming and awkward for diagnostic equipment for which a large throughput is desired.

Surprisingly and unexpectedly, it is not necessary for all applications, to bring the probe reaction product and target complex to releasing conditions, to allow a new set of first and second probes to assume the position of the probe reaction product on the target. Under certain conditions, photoreaction of the photoreactive functional group induces the probe reaction product to leave the target molecule allowing unreacted excess first and second probes to assume a reactive orientation on the target molecule template. A pulsed or continuous supply of radiant energy will produce a plurality of probe reaction products for a single target molecule.

Surprisingly and unexpectedly, the use of photoreactive functional groups on contiguous probes has amplified the signal generated from a single target molecule up to 30-fold. The amplification of signals is generally limited by the generation of side reactions between probe molecules covalently binding to the target template.

Photoreactive functional groups which are sterically impaired from binding to the target molecule template will limit the cross-linking of probes to target and cause further amplification. A preferred photoreactive functional group, coumarin-5-oxybutyric acid N-hydroxysuccinimide ester, does not readily react with the target molecule template.

Further, in the case of polynucleotide target molecules, the selection of target molecules having areas containing few photoreactive nucleotides may further limit the generation of cross-linking reactions to the DNA template. Generally, areas of DNA containing large relative concentrations of pyrimidines may contribute to a higher percentage of cross-linking side reactions between probe and a DNA template.

Additionally, the ability of a polynucleotide probe to leave a DNA target template without pH, ionic or thermocycling, may be related to the generation of thermal energy by the photoreaction between the photoreactive covalent linking functional groups and to some degree by the energies generated by the DNA molecule upon absorbance of radiant energy or steric forces. An embodiment of the present invention includes the introduction of chromophores in close proximity to probes or targets capable of absorbing radiant energy and inducing a localized thermal effect upon the probe reaction product-target complex.

Further processing may include detection of the probe reaction product. For detection of the probe reaction product, one embodiment of the present invention includes the use of a first probe and a second probe where at least one of the probes has a label moiety capable of detection. Preferably, the label moiety is associated with a probe which does not have a capture ligand means for target capture or probe reaction product capture in order to limit background. The probe with the capture means may be captured after steps to photoligate the first and second probe together into a probe reaction product, such that only label moieties, which are associated with the probe reaction product on the second probe, are captured, thereby limiting background noise.

Further processing may also include further amplification beyond the cycling of the probes on the target template to form additional probe reaction product. Thus, one embodiment of the present invention includes the enzymatic multiplication of the probe reaction product which is thereafter detected. Thus, in the situation where the first and second probes are RNA polynucleotides, the enzyme, $Q\beta$ replicase, may be used to produce quantities of an enzyme reaction product based on the presence of the probe reaction product. In the situation where the first and second probes are DNA polynucleotides, the enzyme DNA polymerase may be used to produce quantities of an enzyme product. The enzymatic reaction product can thereafter be detected more readily due to a greater quantity than the probe reaction product.

Amplification can also be performed and when using the probe reaction product as a template, utilizing a second group of probes, antisense to the first probe and the second probe. The second group of probes can be ligated enzymatically or through reactive functional groups. At least one of the second group of probes includes a label moiety capable of detection.

A further embodiment of the present invention includes an apparatus for ligating substantially contiguous ligands which bind to a common target. The apparatus includes a containment vessel for receiving a target and a first ligand and a second ligand. At least one of the first and second ligands has a reactive functional group capable of forming a covalent bond between the first ligand and the second ligand upon activation when the first and second ligands are placed in a reactive position. The first ligand and the second ligand are both capable of simultaneously binding to the target in a reactive position to form a target first-second ligand complex. The apparatus further includes means for activating the reactive functional group to form a covalent bond between the first and second ligands.

Embodiments of the present apparatus have particular application in diagnostics to detect the presence of a target molecule. In one embodiment of the present apparatus, the containment vessel is adapted to receive a first ligand and a second ligand together with a target molecule from a sample. The first ligand and the second ligand have reactive functional groups capable of covalently binding the first probe to the second probe to form a probe reaction product when the reactive functional group is activated and when the first probe and the second probe are in a reactive position. The apparatus further includes means for bringing the first ligand and second ligand into binding conditions with the target molecule. The first ligand and second ligand are capable of forming a ligand reaction product having detectable properties which are distinct from either ligand separately. The apparatus includes activation means to activate the reactive functional group. Activation means may include pH control, light sources, injection of cofactors, and the like. The apparatus further includes detection means for detecting the presence of the ligand reaction product which in turn is indicative of the presence of the target molecule.

A preferred embodiment includes reactive functional groups which are activated with radiant energy. Activation means preferably include a light source having a substantially controlled wavelength corresponding to the activation wavelength of the photoreactive functional groups. Thus, in the situation wherein the photoreactive functional groups have activation energies of approximately 300–380 nm inclusive, preferred activation means include helium-cadmium laser, nitrogen laser, mercury arc lamp or other light sources equipped with appropriate filters.

Embodiments of the present apparatus are adapted to receive crude samples and process the sample to release the target receptor molecule. Further embodiments feature means to capture the target receptor molecule and means for capturing background noise. Still further embodiments feature means for amplifying the probe reaction product or the target to improve signal. The term "crude sample" is used to include clinical samples, including by way of example, biopsy or tissue samples, sputum, blood, excretion, swabs, cultures; agricultural samples, including plant matter soil samples; and industrial samples, including fermentation samples, food and plant material, and the like.

Thus, one embodiment of the present apparatus includes means for receiving a crude sample for sample processing. Sample processing may include dissolution of the sample in chaotropic solutions, alkali, or sonification to release the polynucleotide target molecule from cellular constituents. The apparatus further includes means for receiving a first probe and a second probe. At least one of the first and second probes has a photoreactive functional group capable of forming a covalent bond between the first probe and the second probe in the presence of radiant energy when the first and second probes are placed in a reactive orientation to form a probe reaction product. The first probe and the second probe are capable of simultaneously binding to the polynucleotide target molecule in a reactive position to form a target first-second probe complex. The apparatus further includes means for bringing the probes into binding conditions with the target molecule in order that they may assume the reactive orientation. The apparatus further includes photoligation means for activating the photoreactive functional group with radiant energy as the probes are in the reactive position. The apparatus further includes support means for capturing the probe reaction product. At least one of the probes include capture ligands for binding to a solid support. The apparatus further includes means for segregating cellular debris from the target. Means for segregating cellular debris from the target include, by way of example, apparatus to perform washes and other purging means directed at the cellular debris without disturbing the probe reaction product. The apparatus may also include detection means for detecting the probe reaction product which is indicative of the presence of the target molecule.

One embodiment of the present apparatus features capture ligands which capture reactive functional groups. Upon activation, the capture reactive functional group forms a covalent bond between the solid support and the probe reaction product. The covalent bond between the solid support and the probe reaction product allows more stringent washes and purges. The removal of additional cellular debris from the probe reaction product reduces background noise.

A further embodiment of the present invention features a retrievable support. The retrievable support is in association or capable of associating via capture ligands with one of the first or second probes to the exclusion of the other. The retrievable support is capable of a substantially homogeneous dispersion within a sample medium and mimics in solution kinetics. The support may take many forms including, by way of example, nitrocellulose reduced to particulate form, beads or other particle-like material. Nitrocellulose may be retrieved upon passing the sample medium containing the nitrocellulose support through a sieve. Nitrocellulose may also be impregnated with magnetic particles or the like which would allow the nitrocellulose to migrate within the sample medium upon the application of a magnetic field. Beads or particles may be filtered upon passing the sample through a sieve. Beads or particles may also exhibit electromagnetic properties which would allow the beads or particles to migrate within the sample medium upon the application of a magnetic field. Beads, such as polystyrene beads, may partition to the surface of an aqueous medium due to their respective densities.

Retrievable supports which are adapted to capture an unlabeled probe are used to effect target capture or probe reaction product capture. Retrievable supports which are adapted to capture a labeled probe are used to capture background noise in the form of labeled probe which is not part of the probe reaction product.

A further embodiment of the present invention includes compositions with utility as photoreactive functional groups. Preferred compositions include derivatives of coumarin. Preferably, the coumarin derivative includes a hydroxy or methoxy group at positions 5 or 7 in conjunction with the alpha beta unsaturated lactone functionality to give a 5-hydroxy or methoxy-coumarin or a 7-hydroxy or methoxy-coumarin having significant absorbance at about 320 nanometers.

Preferably, the coumarin derivative has a substituent grouping on the benzene ring for reacting with a ligand reactive functional group. Thus, 5-hydroxy-coumarin and 7-hydroxy-coumarin are derivatized by alkylation with a methylene chain, which chain has an N-hydroxysuccinimide ester group, a group which is known to react with aliphatic amino groups in an aqueous solution. The N-hydroxysuccinimide ester can be reacted with an aliphatic amino group on the ligand. Other amine reactive groups include by way of example, isothiocyanate, sulfonic acid chlorides, carboxylic acids, bromoalkyls, dichlorotriazines and aldehydes, p-nitrophenyl esters, pentachlorophenyl esters and imidates.

Preferably, the methylene chain includes from between 1 to 10 atoms inclusive; and, most preferably, the methylene chain is 3 atoms in length. The methylene chain may include atoms other than carbon, including by way of example, oxygen and nitrogen. The methylene chain of the coumarin is able to react with functionalized DNA to form a linkage. The linkages allow the coumarin derivatives sufficient freedom of motion to orient properly for photo-addition as set forth previously.

A further embodiment of the present invention includes a polynucleotide having a photoreactive functional group selected from the group of photoreactive functional groups consisting essentially of benzo-alpha-pyrones, psoralens, anthracene, pyrene, carotenes, and conjugated polyolefins characterized by conjugated double bonds and ketone functionalities and derivatives thereof. Preferably, the coumarins are selected from the group of coumarins having the structural formula set forth below:

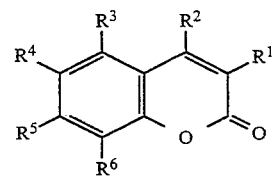

wherein the R groups 1–6 are selected from the groups consisting of —H, —OH, —CH$_3$, —CH$_2$Cl, —CH$_2$Br, —CH$_2$I, —CH$_2$F, —CHBr$_2$, —CHCl$_2$, —CHF$_2$, —CHI$_2$, —CH$_2$OH, —CH$_2$NH$_2$, —N$_3$COOH, —COOCH$_3$, —COOCH$_2$CH$_3$, —NH$_2$, —NO$_2$, —CBr$_3$, —CI$_3$, —CF$_3$, —CCl$_3$, —CH(CH$_3$)$_2$, —O(CH$_2$)$_n$CH$_3$(n=0 to 10), —C(CH$_3$)$_3$, —Cl, —Br, —I, and —F.

Preferably, the psoralens have the general formula set forth below:

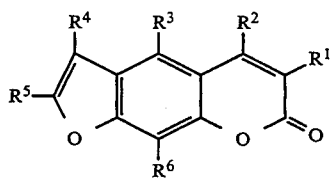

wherein $R_1$ through $R_6$ respectively are selected from the group consisting of for example, —H, —CH$_3$, —CH$_2$Cl, —CH$_2$Br, —CH$_3$I, —CH$_2$F, —CHBr$_2$, —CHCl$_2$, —CHF$_2$, —CHI$_2$, —CH$_2$OH, —CH$_2$OCH$_3$, —CH$_2$NH$_2$, —N$_3$COOH, —COOCH$_3$, —COOCH$_2$CH$_3$, —O(CH$_2$)$_n$CH$_3$(n=0 to 10), —NH$_2$, —NO$_2$, —CBr$_3$, —CI$_3$, —CF$_3$, —CC$_3$, —CH(CH$_3$)$_2$, —C(CH$_3$)$_3$, —Cl, —Br, —I, —F.

Preferred coumarin derivatives include coumarin-7-oxybutyric acid N-hydroxysuccinimide ester, 4-methyl-coumarin-7-oxybutyric acid N-hydroxysuccinimide ester, 7-methoxycoumarin-6-oxybutyric acid N-hydroxysuccinimide ester, and coumarin-6-isothiocyanate. A further embodiment of the present invention includes a composition comprising the reaction product of a reaction of two polynucleotide strands covalently bonded by a derivative of a photoreactive functional group at the 3' and 5' termini of the respective strands.

A further embodiment of the present invention includes a composition comprising a modified polynucleotide having a first strand and a second strand each having a 3' terminal end and a 5' terminal end, the 3' terminal end of one strand bonded to the 5' terminal end of the other strand through dimer, formed from a photoreactive monomer.

A further embodiment of the present invention includes a kit for performing photoligation of contiguous ligands to a target molecule. As applied to diagnostics, where the target molecule is a polynucleotide, the kit includes a reagent for contacting a sample potentially containing a target molecule of interest. The reagent includes a first probe and a second probe wherein the first probe and the second probe have at least one photoreactive functional group, capable of covalently binding the first probe and the second probe to form a probe reaction product in the presence of radiant energy to form a probe reaction product when the first probe and the second probe are placed in a reactive position. The first probe and the second probe are capable of binding to the target molecule to assume a reactive position. The probe reaction product has detectable features which are distinguishable from either the first probe or the second probe individually.

Embodiments of the present invention are simple in construction and in procedure. Embodiments of the present invention are particularly applicable to DNA probe diagnostics and nonradioactive probe labels. Further, the method steps of covalently ligating substantially contiguous probes by means of photoreactive functional groups is applicable to a wide variety of steps and procedures.

Other features and advantages of the present invention will be apparent from the following description, which, by way of illustration, shows preferred embodiments of the present invention and the principals thereof and what is now considered to be the best mode to apply these principals.

DESCRIPTION OF THE DRAWINGS

FIG. 1 illustrates method steps and features of an apparatus and in accordance with embodiments of the present invention in schematic form.

DETAILED DESCRIPTION

The present invention is described in detail as a method and apparatus for ligating contiguous polynucleotide probes to a polynucleotide target molecule of interest in the context of a DNA probe diagnostic apparatus, with the understanding that the present disclosure is to be considered an exemplification of the principals of the invention and is not intended to limit the invention to the embodiment illustrated. The present invention can be used wherever it is necessary to covalently bind two contiguous ligand molecules to form a ligand reaction product upon a template antiligand. For example, the present methods and apparatus have an application in immunodiagnostics, nucleotide synthesis, and sequencing.

Turning now to FIG. 1 of the drawings, a method and apparatus for producing photoligation of substantially contiguous ligands is illustrated with special application for diagnostic purposes to detect a polynucleotide target molecule.

FIG. 1 illustrates in schematic form methods and apparatus for performing an assay in which the assay instrument is generally designated by the numeral 11. The instrument 11 includes the following major components: a containment vessel 13, conveying means illustrated schematically as a double arrow, means for denaturing the target polynucleotide 17, means for bringing the target polynucleotide and a first and a second probe into hybridization conditions 19, means for producing radiant energy within the containment vessel 21, and detection means 23.

As illustrated in FIG. 1, the apparatus is divided into seven stages. Turning now to Stage 1 of FIG. 1, a containment vessel 13 receives a clinical sample containing cells which potentially contain a polynucleotide target molecule. The cells potentially carry target nucleic acid, either DNA or RNA, having a base sequence of particular interest indicative of pathogens, genetic conditions or desirable gene characteristics. Polynucleotide sequences can be identified for the following respiratory infections, diarrhoeas, venereal diseases, sepsis, and food hygiene.

Respiratory infections (a) Bacteria: β-hemolytic streptococci (group A), Hemophilus influenzae, pneumococci, Mycoplasma pneumonlae, mycobacteria (b) Viruses: influenza A, influenza B, parainfluenza (types 1, 2 and 3), respiratory syncytial virus, adenoviruses, coronaviruses, rhinoviruses Diarrhoeas (a) Bacteria: salmonellae, shigellae, Yersinia enterocolitica, E. coli, Clostridium difficile, campylobacter (b) Viruses: rotaviruses, parvoviruses, adenoviruses, enteroviruses Venereal diseases (a) Bacteria: Neisseria gonorrhoeae, Treponema pallidum, Chlamydia trachomatis (b) Viruses: Herpes simplex virus, acquired immune deficiency syndrome (AIDS) virus (c) Yeasts: Candida albicans (d) Protozoa: Trichomonas vaginalis Sepsis (a) Bacteria: β-hemolytic streptococci (group A), pneumocci, enterobacteria Food hygiene:

(a) Bacteria: salmonellae and *Clostridium perfringens.*

The clinical samples may be obtained from any excreta or physiological fluid, such as stool, urine, sputum, pus, serum, plasma, ocular lens fluid, spinal fluid, lymph, genital washings, or the like. Individuals skilled in the art may desire to reduce the biopsy samples to single cell suspensions or small clumps by means known in the art. For example, biopsy samples of solid tissues can be effectively reduced to single cell suspensions or to small clumps of cells by agitating the biopsy sample in a mixture of 0.5 molar sodium chloride, 10 mM magnesium chloride, 0.14 molar phosphate buffer (pH 6.8), and 25 milligrams per milliliter cyclohexamide. Isolation of specific cell types by established procedures known in the art, such as differential centrifugation, density gradient centrifugation, or other methods can also be applied at this stage.

The cells are then treated to liberate their DNA and/or RNA. Chemical lysing is well-known in the art. Chemical lysing can be performed with dilute aqueous alkali, for example 0.1 to 1 molar sodium hydroxide. The alkali also serves to denature the DNA or RNA. Other denaturization in lysing agents include elevated temperatures, organic reagents, for example, alcohols, amides, amines, ureas, phenols and sulfoxides, or certain inorganic ions, for example, chaotropic salts such as sodium trifluoroacetate, sodium trichloroacetate, sodium perchlorate, guanidinum isothiocyanate, sodium iodide, potassium iodide, sodium isothiocyanate, and potassium isothiocyanate.

The clinical sample may also be subjected to various restriction endonucleases to divide the DNA or RNA into discrete segments which may be easier to handle. At the completion of the sample processing steps, the clinical sample includes sample nucleic acid, cellular debris and impurities.

Further reagents include a first probe and a second probe. The first probe and the second probe have photoreactive functional groups capable of covalently binding the first probe and the second probe together to form a probe reaction product upon photoactivation when the first probe and the second probe are in a reactive position. The first probe and the second probe assume a reactive position upon binding to the target molecule to form a target first-second probe complex. When the target molecule is not present, the probes will not be in reaction position. Thus, the formation of the probe reaction product is indicative of the presence of the target molecule.

Those skilled in the art will recognize that the order of addition to the sample of dissolution solvents and first and second probes is arbitrary. Care must be taken, however, that the first and second probes are compatible with the agents used to solubilize cellular material.

At the completion of Stage 1, the sample, which has been processed to liberate the polynucleotide target molecule, is moved to Stage 2 by conveying means. As used here, conveying means includes an endless belt, turntable, or manual movement between areas where different steps of the present method are carried out. Turning now to Stage 2, one embodiment of the present invention includes steps and apparatus to capture the target nucleic acid with a support, in association or capable of associating, with a capture probe. Target capture steps may not be necessary and are optional.

The capture probe may be a separate probe or may include features of a probe participating in reaction in cooperation with another probe and may remain with the target as a first or a second probe. Thus, the capture probe may include a photoreactive functional group capable of covalently binding to a second probe in the presence of light.

The probe moiety may be associated to the support, or capable of association with the support, by covalent bonds between the probe moiety with the retrievable support, by affinity association of the probe to the retrievable support, by hydrogen bonding of the probe moiety to the retrievable support, or by nonspecific association of the probe moiety to the retrievable support. As described herein, the first probe includes a homopolymer tail portion capable of binding to a complementary homopolymer tail associated with a retrievable support and will also participate in photoreactions with a second probe.

The retrievable support may take many forms including, by way of example, nitrocellulose reduced to particulate form and retrievable upon passing the sample medium containing the support through a sieve; nitrocellulose or like materials impregnated with magnetic particles, to allow the nitrocellulose to migrate within the sample medium upon the application of a magnetic field; beads or particles which may be filtered or exhibit electromagnetic properties; and polystyrene beads which partition to the surface of an aqueous medium.

A preferred embodiment of the present invention includes a retrievable support comprising magnetic beads characterized in their ability to be substantially homogeneously dispersed in the Sample medium. Preferably, the magnetic beads contain primary amine functional groups which facilitate covalent binding association of a homopolymer tail portion to the magnetic support particles.

Preferably, the magnetic bead supports are single domain magnets and are super paramagnetic exhibiting no residual magnetism. The particles or beads may be comprised of magnet-type particles, although they can also be other magnetic metal or metal oxides, whether in impure, alloy, or composite form, as long as they have a reactive surface and exhibit an ability to react to a magnetic field. Other materials that may be used individually or in combination with iron include, but are not limited to, cobalt, nickel, and silicon. Methods of making magnetic or metal oxide particles are disclosed in Vandenberghe et al., "Preparation and Magnetic Properties of Ultra-Fine Cobalt Ferrites," *J. of Magnetism and Magnetic Materials,* 15-18:1117-18 (1980); E. Matijevic, "Mono Dispersed Metal (Hydrous) Oxide—A Fascinating Field of Colloidal Science," *Acc. Chem. Res.,* 14:22-29 (1981) the disclosures of which are incorporated herein by reference. A magnetic bead suitable for application to the present invention includes a magnetic bead containing primary amine functional groups marketed under the trade name Bio-Mag by Advanced Magnetics, Inc.

A preferred magnetic particle is nonporous yet still permits association with a probe moiety. Reactive sites not involved in the association of the probe moiety are preferably blocked to prevent nonspecific binding of other reagents, impurities, and cellular material. The magnetic particles preferably exist at substantially colloidal suspensions. Probe moieties associated with the surface of the particle extend directly into solution surrounding the particle. Probe moieties react with dissolved reagents and substrates in solution with rates and yields characteristic of reactions in solutions. Further, with decreasing particle size, the ratio of surface area to volume of the particles increase, thereby permitting more functional groups and probes to be attached per unit weight of magnetic particles.

Beads having reactive amine functional groups can be reacted with polynucleotides to covalently affix the polynucleotide to the bead. The beads are reacted with 10% glutaraldehyde and sodium phosphate buffer and subsequently reacted in a phosphate buffer with an ethylene diamine adduct of the phosphorylated polynucleotide.

The retrievable support with associated homopolymer capture anti-ligand is brought into contact with the processed sample and first probe, and brought into binding conditions. The first probe is specific for the target of interest and becomes bonded to the target strands present in the clinical sample. The retrievable support dispersed throughout the sample and the reagent medium allows the first probe, the target, and the homopolymer tails of the first probe and the support to hybridize as though they were free in solution.

The hybridization of the probe to target can be accomplished in approximately 15 minutes. In contrast, hybridizations in which either the probe or the target are immobilized on the support not having the capability to be dispersed in the medium may take as long as 3-48 hours. Extraneous DNA, RNA, cellular debris and impurities are not specifically bonded to the support. However, as a practical matter, a small amount of extraneous DNA, RNA, cellular debris, and impurities are able, and do in fact nonspecifically bind, to any entity placed within the reaction vessel including the retrievable support.

In one embodiment of the present invention, the support is immobilized within the containment vessel by the introduction of a magnetic field. The support carrying the capture probe and target is isolated from the remaining sample including extraneous DNA, RNA, cellular debris, and impurities.

Thereafter, the target molecule is conveyed to Stage 3 within the same containment vessel 13 or a new containment vessel adapted to receive photoligation reagents, including a first probe and a second probe if such reagents have not already been added. The first probe and the second probe have at least one photoreactive functional group capable of covalently binding the first probe and the second probe to form a probe reaction product in the presence of light when the first probe and the second probe are placed in a reactive position. The first and second probe are capable of binding to the target molecule in a reactive position to form a target first-second probe complex.

The sample target and the first probe and the second probe are placed into binding conditions at Stage 3 by denaturing the polynucleotides carried on the support and photoligation reagents by means of a heating element 17. After the sample target has been denatured at Stage 3, the support, potentially carrying nonspecifically bound extraneous DNA, RNA cellular debris, and impurities is removed.

Next, the containment vessel 13 is conveyed via conveying means to Stage 4 and brought into binding conditions by cooling. Those skilled in the art will recognize that the heating and cooling depicted in Stages 3 and 4 can also be accomplished by pH control, ionic strength and other means to denature and renature the target DNA with the first and second probes.

The target, if present, bound to a first probe and a second probe, which include at least one photoreactive functional group capable of covalently binding the first and second probe to form a probe reaction product, is conveyed to Stage 5.

At Stage 5, the target molecule, if present, and the first and second probe bound in a reactive position, is subjected to radiant energy from a light source including a mercury arc lamp, or a nitrogen laser or a helium cadmium laser. In the presence of the radiant energy, a probe reaction product is formed.

Sufficient energy may be absorbed by the probe reaction product such that the probe reaction product will leave the target template. The target template is capable of binding to a further first probe and second probe and, such additional first probe and second probe are capable of forming a further probe reaction product. Thus, embodiments of the present invention allow additional probe reaction products to be formed from a single target molecule amplifying the signal generated from a single target molecule.

Alternatively, the probe reaction product can be removed from the target template by denaturing the target-probe reaction product complex. In the presence of excess first and second probe, an additional first probe and second probe may assume reactive positions on the target. Upon renaturing and activation, further probe reaction product is formed from a single target molecule. The cycle may be repeated as desired.

The second probe includes a label moiety capable of detection. Preferred fluorescent label moieties include, by way of example, without limitation, fluorescein isothiocyanate, sulforhodamine 101 sulfonic acid chloride (Texas Red), N-hydroxysuccinimidyl pyrenebutanoate, eosin isothiocyanate, erythrosin isothiocyanate, and derivatives thereof. Preferred chemiluminescent agents and cofactors include luminol, microperoxidase, glucose oxidase, acridinium esters, lucigenin, luciferase and derivatives thereof. A preferred color indicating agent includes biotin-avidin-horseradish peroxidase systems. Stage 6 provides for isolation of the probe reaction product and, if necessary, background capture in order to improve the signal-to-noise ratio of the detection system. Isolation of the probe reaction product can be accomplished by capture of the first probe ligand on a support, gel separation, and the like. Further, purificaiton of probe reaction product may be achieved by cycles of capture and release of the probe reaction product from a support to remove nonspecific cell, bound labeled probe material.

Preferably, Stage 6 provides for a means to capture labeled second probe which is not part of the photoligation probe reaction product. Suitable means for removing unligated labeled probe include, by way of example without limitation, enzymatic destruction of the labeled probe apart from the probe reaction product, physical removal of the labeled probe upon a support having a specific ligand for the labeled probe apart from the probe reaction product.

From Stage 6, probe reaction product is moved to Stage 7 via conveying means where the label moiety on the labeled probe as part of the probe reaction product is detected. For some detection systems it may be advantageous to remove the probe reaction product from the support. In the event that the label moiety is a fluorophore, the detection means include means to excite one of the label moieties, for example, a laser having an appropriate emission spectrum corresponding to the excitation spectrum of the label moiety, or a light source equipped with suitable filters. In the event that the label moieties include a chemiluminescent agent, the excitation means would include means for injecting into the containment vessel 13 suitable cofactors to produce a light emitting reaction. For label moieties which produce a light signal, such as chemiluminescent label moieties or fluorescent label moieties, Stage 7 includes a signal detector 23 in the form of a photon counter positioned to receive fluorescent emissions or chemiluminescent emissions from the containment vessels. The photon counters produce a photon signal which is received, amplified, and processed by an analyzer. The analyzer processes the photon signals into values which can be graphically depicted or rendered into other forms which convey the results to an operator.

In the event that the label moiety is a colorimetric label moiety, such as a biotin-avidin system in which the hybridized biotinylated probe is detected enzymatically, detection is based on the binding of biotin to strept-avidin where typically a preformed strept-avidin, horseradish peroxidase complex is used to recognize and bind to a biotin moiety associated with the DNA probe. The presence of the biotinylated probe is determined by the addition of peroxidase substrates which yields a colored precipitate.

Embodiments of the present apparatus for the detection of target molecules of interest are compatible with cycling between Stage 5 and Stage 3 to produce greater quantities of probe reaction products. The cycling may include the addition of a second set of probes. The second set of probes can be used which bind to the first probe reaction product to form a second probe reaction product. The second set of probes contains a label moiety capable of detection. The denaturization and hybridization cycles with a second probe set to the probe reaction product can provide an exponential increase in total detectable signal. The photoligated product of each probe set is capable of serving as a template for the ligation of the other probe set which is initiated by the presence of the target molecule.

The present apparatus is further compatible with other means of amplification. Other means of amplification include enzymatic generation of target molecules by means of RNA polymerase, DNA polymerase, and other enzymatic means of amplification. In a situation where the ultimate goal is to detect a pathogen, such as a virus or bacteria, it may be advantageous to select a target molecule apart from the genomic DNA due to a higher copy number. Thus, the embodiments of the present invention are adapted for use in searching for ribosomal RNA or messenger RNA which can be further amplified using $Q\beta$ replicase as suggested in *Methods in Enzymology* (1979), 60:628. The replication product produced by $Q\beta$ replicase can be a further template for the enzyme producing an RNA target which is replicated exponentially.

The present invention is further illustrated and described in the following experimental examples which exemplify features of the preferred embodiments.

EXAMPLE 1

A. Overview

Example 1 describes preferred synthesis of photoreactive molecules, which can be reacted with probe molecules, particularly polynucleotides, to form polynucleotide probes having photoreactive functional groups. The photoreactive molecule includes a chromophore and a reactive group. Preferably, the reactive group is reacted with the polynucleotide probes by chemistry which is nondisruptive of features essential to its operation as a probe. Suitable reactive groups include N-hydroxysuccinimide ester, isothiocyanate, sulfonic acid chlorides, carboxylic acids, bromo alkyls, dichlorotriazines, aldehydes, p-nitrophenyl esters, pentachlorophenyl esters and imidates which are known to react with aliphatic amine groups.

Preferably, the probe molecules include a reactive methylene chain which will react with the reactive group of the photoreactive molecule. A preferred reactive methylene chain includes an aliphatic chain of 1 to 10 atoms. The probe methylene chain may include atoms other than carbon, including by way of example, oxygen and nitrogen. The terminal atom is preferably an amine. The probe methylene chain, with the reactive group of the photoreactive molecule form a linkage.

The length of the linkage will influence the ability of the photoreactive groups to orientate for a 2+2 cycloaddition reaction. Further, the length of the covalent linkage to the probe may sterically impede the interaction of the photoreactive group with hybridized nucleotide bases.

Preferably, the photoreactive group is amenable to 2+2 cycloaddition. Preferred photoreactive groups have excitation energies compatible with available radiant energy sources. Preferred excitation energies include 325 nm and 337 nm corresponding to the wavelength of emissions from a helium-cadmium laser and a nitrogen gas laser respectively and the 300–400 nm region of a mercury arc lamp. Preferred photoreactive groups have a significant extinction coefficient of not less than 000 mole $^{-1}\cdot$cm$^{-1}$ to permit efficient excitation.

Preferably, photoreactive groups selectively react with specific photoreactive groups, and not with nucleotide bases, to provide covalent irreversible dimerisation. Preferred photoreactive groups include coumarin derivatives, including by way of example, without limitation, coumarin-7-oxybutyric acid N-hydroxysuccinimide ester, 4-methylcoumarin-7-oxybutyric acid N-hydroxysuccinimide ester, 7-methoxycoumarin-6-oxybutyric acid N-hydroxysuccinimide ester, coumarin-5-oxybutyric N-hydroxysuccinimide ester, 6-methoxycoumarin-7-oxybutyric acid N-hydroxysuccinimide ester, and coumarin-6-isothiocyanate.

Reaction Scheme 1, set forth below, generally describes the synthesis of a photoreactive molecule capable of reacting with a functionalized DNA.

Scheme 1

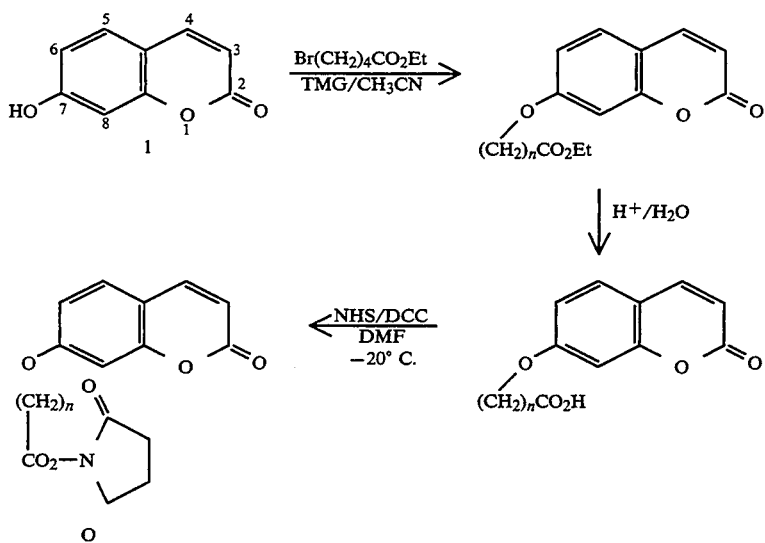

As used above, n may be an integer 1 to 10. However, when n equals 1, photoreactive molecules capable of reacting in the functional DNA exhibit limited stability. A preferred integer is three.

For the synthesis of coumarin-7-oxybutyric acid N-hydroxysuccinimide ester, n equals 3 and $R_1$ equals hydrogen. For the synthesis of 4-methylcoumarin-7-oxybutyric acid N-hydroxysuccinimide ester, n equals 3 and $R_1$ equals methyl.

In reaction Scheme 1, a coumarin or coumarin derivative is first alkylated with an alkylating agent, having an aliphatic group of a preferred number of carbons, in refluxing acetonitrile solution in the presence of a strong base, such as $N^1$, $N^1$, $N^3$, $N^3$-tetramethylguanidine to form an ethyl ester derivative. The ethyl ester derivative is then hydrolysed with aqueous strong acid, such as hydrochloric acid, in acetone. Reaction Scheme 2, set forth below, generally describes the synthesis of 7-methoxy derivatives of coumarin beginning with a 7-hydroxy coumarin derivative having a blocking group at an oxidized 6 position:

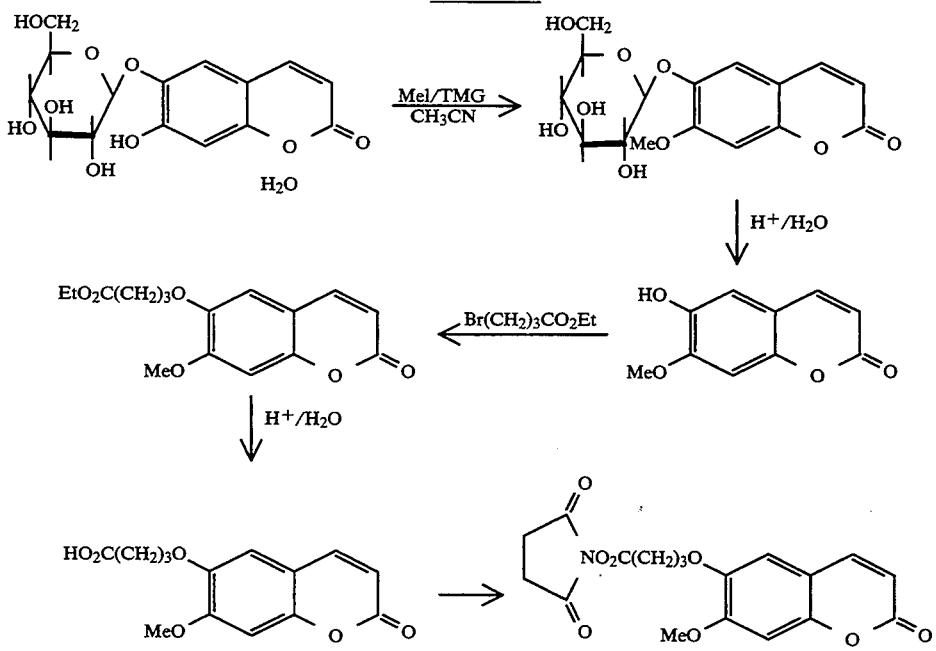

A further reaction scheme, Scheme 3 set forth below, is used to link a coumarin derivative to reactive aliphatic amine on a polynucleotide at the 6 position through an isothiocyanate functional group producing a shorter aliphatic chain between the coumarin derivative and the polynucleotide:

Scheme 3

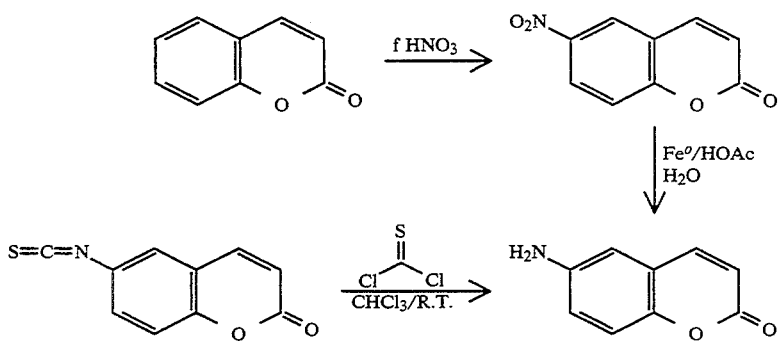

The isothiocyanate derivative is produced by nitrating a coumarin derivative at the 6 position, reducing the nitro to an amine, and reacting the amino derivative with thiophosgen.

Other syntheses of coumarin derivatives which will react with amine derivatized polynucleotides include reactions of hydroxylated derivatives of coumarin with bromoacetonitrile as set forth in Scheme 4 below:

Scheme 4

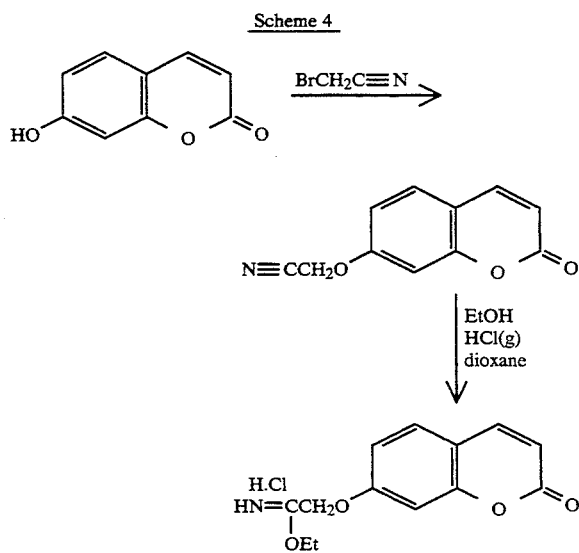

A further synthesis of coumarin derivatives directed to the ring structure is set forth in Scheme 5 below:

Scheme 5

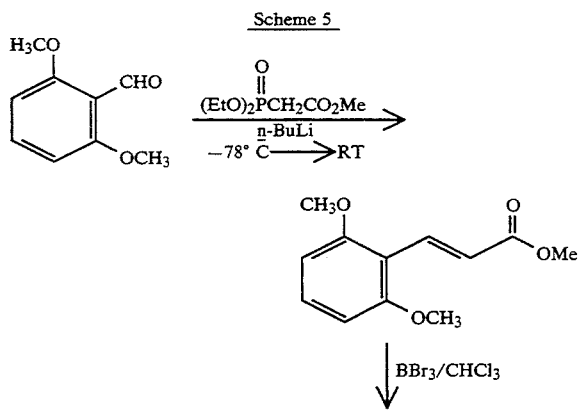

-continued
Scheme 5

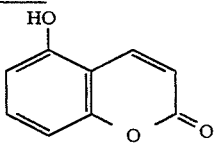

B. Materials and Methods

In the foregoing example, 7-hydroxycoumarin (umbelliferone, [93-35-6]), 7-hydroxy-4-methylcoumarin [90-33-5], esculin monohydrate [531-75-9], 7-hydroxy-6-methoxycoumarin (scopoletin, [92-61-5]), 6-hydroxy-7-methoxycoumarin (isoscopoletin, [776-86-3]) and coumarin [91-64-5] were obtained from Aldrich Chemical Company, Milwaukee, Wis.

Thin-layer chromatography (TLC) was performed on Merck silica gel 60F-254 glass-backed plates. The following solvent systems were used: (A) chloroform-methanol (19:1, v/v); (B) chloroform-methanol (9:1, v/v); (C) chloroform-methanol (4:1, v/v). After development substances were detected by UV light. Fourier transform NMR spectra were obtained on a Nicolet instrument at 300 MHz unless otherwise stated.

Quantitative UV spectra were obtained on a Hewlett Packard 8451A diode array spectrophotometer.

C. Coumarin-7-oxybutyric Acid N-hydroxysuccinimide Ester

Coumarin-7-oxybutyric acid N-hydroxysuccinimide ester was prepared by reacting 7-hydroxycoumarin with ethyl 4-bromobutyrate to form coumarin-7-oxybutyric acid ethyl ester. Next, the ethyl ester was reacted with acid to form coumarin-7-oxybutyric acid which was reacted with N-hydroxysuccinimide to form the N-hydroxysuccinimide ester in accordance with the Scheme 1 above.

To a magnetically stirred mixture of 7-hydroxycoumarin (8.1 g, 50 mmol) and ethyl 4-bromobutyrate (8.0 ml, 55 mmol) in acetonitrile (150 ml) was added in portions, $N^1$, $N^1$, $N^3$, $N^3$,-tetramethylguanidine (TMG 7.0 ml, 55 mmol). The deep yellow solution was heated under reflux for 4 hours, when TLC (System B) indicated a partial conversion to a new higher $R_f$ substance. A further 2.91 ml of ethyl 4-bromobutyrate and 2.55 ml of TMG were added and the mixture heated under reflux for a further 2 hours or until the reaction is complete (TLC). The solvent was evaporated in vacuo, the residue dissolved in chloroform (150 ml), extracted with saturated sodium hydrogen carbonate solution (2×150 ml), dried (MgSO$_4$) and evaporated to a thick oil which slowly solidified. The solid was recrystallized from methanol (25 ml) and then from aqueous methanol. Yield 12.5 g (91%). $^1$H NMR (DMSO-d$_6$): 7.99 (d, J=9.6Hz, 1H), 7.62 (d, J=8Hz, 1H), 6.98 (d, J=2.4Hz, 1H), 6.94 (dd, J=8, 2.4Hz, 1H), 6.29 (d, J=9.6Hz, 1H), 4.08 (m, 4H), 2.47 (t, J=8Hz, 2H), 1.99 (q, J=8Hz, 2H), 1.19 (t, J=8Hz, 3H) M.p. 66°-70° C. UV (Methanol): Lambda max 324 nm (14 700), 290 nm (shoulder), lambda min 260 (1 300).

Coumarin-7-oxybutyric acid ethyl ester, 12.5 g was completely dissolved in acetone (200 ml) and 5M aqueous hydrochloric acid (200 ml) was added. The resulting solution was stirred at room temperature for 20 hours or until the reaction was complete (TLC, System B). The crystals of the coumarin-7-carboxylic acid which had separated from solution were collected by filtration on a sinter glass funnel, washed thoroughly with water and finally with ethanol then dried over P$_2$O$_5$ overnight. Yield 10.11 g (90%). M.p. 198°-200° C. R$_f$(System B) 0.05. $^1$H NMR (DMSO-d$_6$): 7.99 (d, J=9Hz, 1H), 7.62 (d, J=8Hz, 1H), 6.98 (m, 2H), 6.28 (d, J=9Hz, 1H), 4.10 (t, J=5Hz, 2H), 2.40 (t, J=5Hz, 1H), 1.97 (m, 2H).

To a solution of coumarin-7-oxybutyric acid (1.39 g, 5 mmol) and N-hydroxysuccinimide (1.08 g, 5.25 mmol, 1.05 equiv.) in anhydrous pyridine (15 ml), cooled to −35° C. using an ethanol/dry-ice bath, was added dropwise a solution of dicyclohexylcarbodiimide (DCC, 1.08 g, 5.25 mmol, 1.05 equiv.) and the mixture was allowed to warm up to room temperature overnight. TLC (System B) revealed a partial conversion to a new higher R$_f$ substance. To complete the reaction, the mixture was recooled to −35° C. and a further 0.51 g (0.5 equiv.) of DCC, and 0.29 g (0.5 equiv.) of NHS were added. After a further 5 hours, the reaction was complete, excess DCC was quenched by addition of three or four drops of glacial acetic acid and the precipitated dicyclohexylurea removed by filtration. The filtrate was evaporated in vacuo, the residue co-evaporated with toluene (4×30 ml), dissolved in chloroform (50 ml), extracted with saturated sodium hydrogen carbonate (2×40 ml) and finally evaporated to dryness in vacuo to a colorless solid. The solid was co-evaporated a further two times with toluene to remove last traces of pyridine and finally, recrystallized from toluene to give colorless needles of the product. Yield 1.74 g, 100%. M.p. 144°-146° C. $^1$H NMR (DMSO-d$_6$): 7.98 (d J=8hz, 1H) 7.63 (d, J=7Hz, 1H), 6.99 (m, 2H), 6.29 (d, J=7Hz, 1H), 4.17 (t, J=6Hz, 2H), 2.88 (t, J=6Hz, 2H), 2.83 (br s, 4H), 2.11 (quintet, J=6Hz, 2H). The four proton singlet at 2.83 was characteristic of this compound being an NHS-ester.

The activity of the N-hydroxysuccinimide ester was determined by a control experiment in which a 5'-aminopropyl-T10 oligomer was labeled in solution as follows. The oligomer (5 optical density units) was dissolved in 0.2M MOPS buffer, pH 7.2, 0.5 ml and 0.05 ml of a solution of the NHS-ester in DMF (3.9mg, in 0.221 ml DMF, 60 equiv.) was added. The mixture was incubated at 37° C. for 22 hours when analysis on ion-exchange HPLC revealed an 81% conversion to the coumarin-labelled T10 oligomer.

D. Preparation of 4-Methylcoumarin-7-oxybutyric Acid N-hydroxysuccinimide Ester 4-methylcoumarin-7-oxybutyric acid N-hydroxysuccinimide ester was prepared from 7-hydroxy-4-methylcoumarin by a sequence of reactions analogous to those used to prepare coumarin-7-oxybutyric acid N-hydroxysuccinimide ester.

Yield 38% after recrystallization from toluene. M.p. 176°-180° C. $^1$H NMR (DMSO-d$_6$): 7.70 (d, J=8hz, 1H), 6.99 (m, 2H), 6.21 (d, J=2Hz, 1H), 4.17 (t, J=6Hz, 2H), 2.87 (t, J=6Hz, 2H), 2.82 (s, 4H), 2.11 (t, J=6Hz, 2H). R$_f$(System B)=0.65.

E. Preparation of 7-Methoxycoumarin-6-Oxybutyric Acid N-hydroxysuccinimide Ester 7-methoxycoumarin-6-oxybutyric acid N-hydroxysuccinimide ester was prepared in a two part reaction scheme described in Scheme 2.

Part 1. Preparation of 6-hydroxy-7-methoxycoumarin (isoscopoletin).

To a suspension of esculin monohydrate (5.0 g, 13.95 mmol) in acetonitrile (150 ml) containing methyl iodide (3.0 ml, 48.4 mmol, 3.44 equiv.) was added TMG (3.22 g, 28 mmol). Upon heating to reflux temperature the gummy mixture dissolved to give a bright yellow solution, which slowly decolorized and crystals formed in the reaction mixture. After 3 hours the mixture was cooled to room temperature and the crystals collected by filtration, washed with acetonitrile 2×25 ml) and air dried. Yield 3.81 g. The reaction product was not characterized further but used directly in the next step. Thus, the reaction product (3.81 g, 10.7 mmol) was suspended in aqueous sulfuric acid (95:5 H$_2$O/H$_2$SO$_4$, v/v, 60 mls) and the mixture stirred and brought to reflux. After 20 minutes crystals started to form in the reaction mixture. After 1 hour at reflux, the mixture was cooled to room temperature, the crystals removed by filtration, washed with water (2×50 ml) and finally air dried. The crystalline product was identified as 6-hydroxy-7-methoxycoumarin. Yield: 1.87 g (70%). M.p.: 185°-190° C. (lit.,[11] m.p. 185° C. from 40% acetic acid). UV spectrum (Methanol): Lambda max 232(s), 256(w), 348(s).

Part 2. Preparation of 6-hydroxy-7-methoxycoumarin N-hydroxysuccinimide ester.

7-Methoxycoumarin-6-oxybutyric acid N-hydroxysuccinimide ester was prepared in accordance with the protocol set forth previously for coumarin-7-oxybutyric acid ester. First, 7-methoxycoumarin-6-oxybutyric acid ethyl ester was prepared from 6-hydroxy-7-methoxycoumarin in a procedure analogous to the procedure set forth above in regard to coumarin-7-oxybutyric acid ethyl ester. The reaction product, 7-methoxycoumarin-6-oxybutyric acid ethyl ester, was identified and had the following characteristics: $^1$H NMR (DMSO-d$_6$): 7.93 (d, J=9hz, 1H), 7.25 (s, 1H), 7.07 (s, 1H), 6.29 (d, J=9Hz, 1H), 4.07 (quartet, J=7Hz, 2H), 4.01 (t, J=6Hz, 2H), 3.869 (s, 3H), 2.50 (t, J=6Hz, 2H), 1.99 (t, J=7Hz, 3H). UV (methanol) lambda max: 232(17 600), 296(5 800), 344(11 700)nm. M.p. 93°-95° C. (double recrystallization from ethanol). Yield 85%.

The reaction product, 7-methoxycoumarin-6-oxybutyric acid ethyl ester was reacted with acid to form the carboxylic acid, 7-methoxycoumarin-6-oxybutyric acid, in a procedure analogous to the procedure set forth above in regard to coumarin-7-oxybutyric acid. The carboxylic acid had the following characteristics: $^1$H NMR (DMSO-d$_6$): 7.93 (d, J=9hz, 1H), 7.27 (s, 1H), 7.07 (s, 1H), 6.29 (d, J=9Hz, 1H), 4.00 (t, J=7Hz, 2H), 3.87 (s, 3H), 2.40 (t, J=7Hz, 2H), 1.96 (quintet, J=7Hz, 2H). M.p. 188°-191° C. Yield 88%.

The reaction product, 7-methoxy-coumarin-6-oxybutyric acid was reacted with N-hydroxysuccinimide to form 7-methoxycoumarin 6-oxybutyric acid N-hydroxysuccinimide ester in a manner analogous to the procedure to prepare coumarin-7-oxybutyric acid N-hydroxysuccinimide ester with the important difference that the reaction solvent consisted of a 1:1 mixture of DMF and pyridine. The N-hydroxysuccinimide ester had the following characteristics: $^1$H NMR (DMSO-d$_6$) : 7.93 (d, J=9hz, 1H), 7.28 (s, 1H), 7.09 (s, 1H), 6.30 (d, J=9Hz, 1H), 4.08 (t, J=7Hz, 2H), 3.879 (s, 3H), 2.87 (t, J=7Hz, 2H), 2.82 (s, 4H), 2.09 (quintet, J=7Hz, 2H). M.p. 163°–166° C. (recrystallized from toluene with a hot filtration and then from ethyl acetate). Yield 47%.

F. Preparation of 6-Methoxycoumarin-7-Oxybutyric Acid N-Hydroxysuccinimide Ester The compound 6-methoxy-coumarin-7-oxybutyric acid N-hydroxysuccinimide ester was prepared in a manner analogous with the preceding compound, the positional isomer, 7-methoxycoumarin-6-oxybutyric acid N-succinimide ester. The ethyl ester had the following characteristics: $^1$H NMR (DMSO-d$_6$) : 7.95 (d, J=9Hz, 1H), 7.26 (s, 1H), 7.06 (s, 1H), 6.29 (d, J=9Hz, 1H), 4.09 (t, J=6Hz, 2H), 4.07 (quartet, J=6Hz, 2H), 3.81 (s, 3H), 2.49 (t, J=6Hz, 2H), 2.01 (quintet, J=6Hz, 2H), 1.19 (t, J=6Hz, 3H). M.p. 92°–96° C. (recrystallized twice from ethanol).

The compound, 6-methoxycoumarin-7-oxybutyric acid had the following characteristics: $^1$H NMR (DMSO-d$_6$): 7.95 (d, J=9hz, 1H), 7.26 (s, 1H), 7.06 (s, 1H), 6.30 (d, J=9Hz, 1H), 4.09 (t, J=7Hz, 2H), 3.812 (s, 3H), 2.40 (t, J=7Hz, 2H), 1.97 (quintet, J=7Hz, 2H). M.p. 182°–186° C.

The compound 6-methoxycoumarin-7-oxybutyric acid N-hyrdoxysuccinimide had the following characteristics: $^1$H NMR (DMSO-d$_6$): 7.94 (d, J=9Hz, 1H), 7.26 (s, 1H), 7.05 (s, 1H), 6.30 (d, J=9Hz, 1H), 4.10 (t, J=7Hz, 1H) 3.81 (s, 3H), 2.82 (s, 4H), 2.40 (t, J=7Hz, 2H), 1.98 (quintet, J=Hz, 2H).

G. Preparation of Coumarin-6-Isothiocyanate

Coumarin-6-isothiocyanate was prepared in accordance with Scheme 3 above. First, coumarin was nitrated in accordance with the teaching of Delalande, Annalen, 45 p337 (1843), to form 6-nitrocoumarin. The 6-nitrocoumarin was next reduced to 6-aminocoumarin. The 6-aminocoumarin was then reacted with thiophosgene to form coumarin-6-isothiocyanate.

In greater detail, coumarin (10 g, 68 mmol) was nitrated as described in the literature with an excess of fuming nitric acid overnight at room temperature to give 6-nitrocoumarin as the only major product. The 6-nitrocoumarin exhibited the following characteristics: Yield 85%. $^1$H NMR (DMSO-d$_6$): 8.74 (d, J=3Hz, 1H), 8.42 (dd, J=3, 9Hz, 1H), 8.24 (d, J=10Hz, 1H), 7.63 (d, J=9Hz, 1H), 6.70 (d, J=10Hz, 1H).

Next, one portion of the 6-nitrocoumarin product (3.35 g 17.54 mmol) was added to a magnetically stirred mixture of iron powder (8.0 g, excess) suspended in aqueous acetic acid (60 ml, 1:1 v/v). After several minutes an exothermic reaction ensued, which turned the reaction mixture bright yellow. The reaction was allowed to continue without cooling and a reflux condenser was used to control evaporation losses. After 10–15 minutes the reaction mixture was cooled to room temperature with an ice bath and the mixture evaporated to a thick green slurry in vacuo. Taking appropriate precautions with the frothing nature of the reactants, saturated sodium hydrogen carbonate solution (200 ml) was added to the residue and the product was extracted by thorough stirring into ethyl acetate (1×250 ml, 1×100 ml). The combined ethyl acetate extracts were evaporated to dryness to give a bright yellow powder 2.5 g (89%). Water (150 ml) was added to the solid, the mixture brought to reflux, charcoal (2–3 g) was added, the mixture rapidly filtered through a fluted filter paper and allowed to cool. The bright yellow needles of the product were collected, washed with water and dried over P$_2$O$_5$ overnight to produce a yield of 2.14 g 6-aminocoumarin (M.p. 161°–163° C.).

Other characteristics of the reaction product 6-aminocoumarin are set forth below: $^1$H NMR (DMSO-d$_6$): 7.88 (d, J=9.5Hz, 1H), 7.10 (d, J=8.8Hz, 1H), 6.85 (d, J=8.8, 2.7Hz, 1H), 6.73 (d, J=2.7Hz, 1H), 6.73 (d, J=2.7Hz, 1H), 6.35 (d, J=9.5Hz, 1H), 5.25 (broad s, 2H). UV (Methanol) lambda Max: 246(w), 282(m), 370(w).

To a stirred solution of 6-aminocoumarin (0.320 g, 2.0 mmol), triethylamine (1.0 ml, excess) and chloroform (15 ml) was added dropwise, over 5 minutes, thiophosgene (0.22 ml, 2.4 mmol). The reaction was finished after the addition of the thiophosgene was complete. More chloroform (50 ml) was added and the solution was extracted with saturated sodium hydrogen carbonate solution (2×50 ml), followed by water (1×50 ml), then evaporated to an orange solid. The solid was recrystallized from isopropanol, and finally from toluene (hot filtration, no charcoal) to remove a dark insoluble residue. Pale yellow crystals identified as coumarin-6-isothiocyanate (M.p. 189°–191° C.) were obtained.

Other characteristics of the reaction product coumarin-6-isothiocyanate are as follows: $^1$H NMR (CDCl3): 7.64 (d, J=10Hz, 1H), 7.30–7.41 (m, 3H), 6.49 (d, J=10Hz, 1H). UV (methanol): 226(31 700), 268(29 900), 334(4 700)nm. TIR Spectrum (KBr disc): 3100, 2118(strong, N=C=S), 1724(strong, C=S), 1584, 1499, 1288, 1188, 1120, 888, 822 cm$^{-1}$.

H. Preparation of Coumarin-5-oxybutyric Acid N-Hydroxysuccinimide Ester

Coumarin-5-oxybutyric Acid N-hydroxysuccinimide Ester was prepared in accordance with Scheme 5 above. 2,6-dimethoxybenzaldehyde was reacted with methyl diethyl phosphonoacetate and n-butyllithium to form 2,6-dimethoxycinnamic acid methyl ester. The methyl ester was reacted with boron tribromide to form 5-hydroxycoumarin. 5-hydroxycoumarin was reacted with acid to form coumarin-5-oxybutyric acid. The acid was reacted with N-hydroxy-succinimide to form the N-hydroxysuccinimide ester.

In greater detail, a cooled, (−78° C.) magnetically stirred solution of methyl diethyl phosphonoacetate (6.3 g, 30 mmol) in anhydrous tetrahydrofuran (50 ml) was added, in portions over 20 minutes, a solution of n-butyllithium in hexane (20 ml of a 1.3M solution). To the resultant pale-yellow solution was added dropwise a solution of 2,6-dimethoxybenzaldehyde (4.98 g, 30 mmol) in tetrahydrofuran (40 ml). The reaction mixture was allowed to warm to room temperature overnight when TLC revealed the formation of one new major product. The reaction was quenched by the addition of 2M aqueous acetic acid (50 ml), diethyl ether (200 ml) was added, followed by water (200 ml). The organic phase was separated and extracted with saturated sodium hydrogen carbonate solution (200 ml), dried (MgSO$_4$) and evaporated to give a thick oil (5.2 g) which did not crystallize.

The reaction product was further identified as 2,6 dimethoxycinnamic acid methyl ester. $^1$H NMR (CDCl$_3$): 8.14 (d, J=16.1Hz, 1H), 7.26 (t, J=8.4Hz, 1H), 6.89 (d, J=16.2Hz, 1H), 6.55 (d, J=8.4Hz, 2H), 3.88 (s, 6H), 3.80 (s, 3H).

To a cold (−30° C.) solution of 2,6-dimethoxycinnamic acid methyl ester (5.2 g, 23.4 mmol, prepared as described above), in chloroform (250 ml), was added boron tribromide (80 ml of a 1M solution in methylene chloride). The mixture was allowed to stir under anhydrous conditions was poured into saturated aqueous sodium hydrogen carbonate solution (400 ml). [Caution Frothing] The organic phase was diluted with ethyl acetate (250 ml), the mixture was transferred to a separating funnel and extracted thoroughly. The organic phase was isolated, dried (MgSo$_4$) and evaporated in vacuo to give a dark red oil which did not crystallize. The oil was purified further by chromatography on silica gel to give 5-hydroxycoumarin (3.4 g, 89%), as a pale-yellow crystalline powder. M.p. 226°–229 ° C. (Das Gupta et al. J. Chem. Soc. (C), 29, 1969 give m.p. 224°–225° C.) $^1$H NMR (DMSO-d$_6$): 8.11 (dd, J=9,6,0.6Hz, 1H), 7.40 (t, J=8.4Hz, 1H), 6.78 (m, 2H), 6.34 (d, J=9.6Hz, 1H).

5-Hydroxycoumarin was converted to coumarin-5-oxybutyric acid N-hydroxysuccinimide ester by the three step procedure described for the isomeric 7-hydroxycoumarin.

Coumarin-5-oxybutyric acid N-hydroxysuccinimide ester was obtained as an oil that did not crystallize. $^1$H/NMR (DMSO-d$_6$): 8.19 (dd, J=9.6,0.6Hz, 1H), 7.55 (t, J=8.4Hz, 1H), 6.97 (d, J=8.4Hz, 1H), 6.93 (dd, J=8.4,0.6Hz, 1H), 6.39 (d, J=9.6Hz, 1H), 4.21 (t, J=6.6Hz, 2H), 2.96 (t, J=7.2Hz, 2H), 2.82 (s, 4H), 2.17 (q, J=7.2Hz, 2H).

EXAMPLE 2

DNA Synthesis

All chemically synthesized DNA was prepared on an Applied Biosystems 370B Synthesizer using reagents and phosphoramidites supplied by the manufacturer. The crude synthetic DNA was purified on a reverse phase column using a Pharmacia fast protein liquid chromatography (FPLC) system, using a liquid chromatography controller LCC-500, pump P-500, single path monitor UV-1 and fraction collector FRAC-100. The crude, detritylated DNA obtained from the synthesizer (80–100 OD units), dissolved in water (0.5 ml) was purified on a PEP RPC C18 column eluted with 10 mmol triethylammonium acetate which was supplemented (0.75–1.00% per min.) with 10 mmol triethylammonium acetate-acetonitrile (1:1, v/v). The eluent was pumped at a rate of 1 ml/min. and 2 ml fractions were collected. The appropriate fractions were pooled and evaporated to dryness using a Savant centrifugal vacuum concentrator and the sample homogeneity analyzed by HPLC on a Hewlett-Packard 1090 liquid chromatogram using a C-4 column eluted with 0.1M triethylammonium acetate, pH 7.24, supplemented (0.5% per min.), with acetonitrile. The yield of recovered DNA was typically around 50%.

A 30-mer sequence of the enterotoxin gene of *E. Coli* was chosen as target. The target sequence is set forth below:

Target- 5' TTG GTG ATC CGG TGG GAA ACC TGC TAA TCT 3' was synthesized chemically. A first and a second probe were also synthesized chemically having base sequences as set forth below:

Probe 1-5'GGA TCA CCA A 3'
Probe 2-5'AGA TTA GCA GGT TTC CCA CC 3'.

The first probe was 5'end-labeled with one of the coumarin derivatives and 3' end labeled with $^{32}$P. The second probe was 3'end-labeled with one of the coumarin derivatives. The first and the second probe are capable of binding to contiguous portions of the target molecule.

In greater detail, the first probe was prepared by initially synthesizing a 9-mer oligomer (minus the 3'terminal base in the above sequence) which was 5'end-labeled with (3-(N-trifluoroacetylaminopropyl)) methyl-N,N-diisopropyl phosphoramidite (TFAAMDIIPP). The following protocol is typical, beginning with the synthesis of the phosphoramidite.

To a dry 100 ml three-neck round bottom flask equipped with stir bar and reflux condenser was added anhydrous methanol (10 ml) and ethyl trifluoroacetate (12.5 g, 0.17 mol). The resulting mixture was stirred at room temperature and 3-amino-1-propanol (12.5 g, 0.17 mol) was added slowly. The reaction mixture started to boil shortly after the addition of 3-amino-1-propanol. After 18 hours the mixture was evaporated under reduced pressure to yield a clear viscous oil. The product was purified by vacuum distillation. Yield=24.0 g, 85% (BP=85°–86° C. 0.25 mm Hg).

A dry 200 ml three-neck round bottom flask was equipped with a magnetic stir bar, sealed with rubber septa and purged with dry nitrogen. To the flask was added 3-(N-trifluoroacetylamino)-1-propanol (6.06 g, 35 mmol), diisopropylethylamine (36.1 g, 280 mmol) 50 ml and dry THF (30 ml). The mixture was stirred and cooled to 0° C. A solution of diisopropyl methyl phosphonamidic chloride (5.5 g, 28 mmol) in tetrahydrofuran (50 ml) was then added dropwise to the cooled reaction mixture. After a few minutes, a white precipitate was observed. Stirring was continued for a total of 1.5 hours after which time the hydrochloride salt was removed by vacuum filtration and the mixture was washed with 5% NaHCO$_3$ (3×50 ml). The organic layer was collected, dried over sodium sulfate, filtered and then evaporated under reduced pressure. The resulting product was dissolved in a mixture of ethyl acetate/triethylamine 9/1 v/v (10 ml) and applied to a column of silica gel (1½"×8"). The column was eluted with the same solvent mixture. Fractions (30 ml) were collected. Those fractions (8–13) which contained the desired product were pooled, transferred to a separatory funnel and washed with 5% NaCO$_3$ (2×100 ml). The organic portion was then dried over sodium sulfate and evaporated to yield a slightly yellow colored oil which was co-evaporated with toluene (2×10 ml) to yield 9.25 g of purified product (55%). The product was identified as (3-(N-trifluoroacetylaminopropyl)) methyl-N,N-diisopropyl phosphoramidite.

A standard Applied Biosystems DNA synthesis protocol was used on an Applied Biosystems 370B DNA synthesis machine. The synthesis protocol included the standard acid deblocking, phosphorylation, capping and oxidation steps. Once the desired probe nucleic acid sequence was synthesized, one additional cycle was completed in which the new phosphoramidite, (3-(N-trifluoroacetylaminopropyl)) methyl-N,N-diisopropyl phosphoramidite was used in order to add the protected aminopropyl group to the 5' end of the protected oligonucleotide chain. The resulting oligonucleotide was recovered after deblocking with thiophenol and/or ammonium hydroxide according to the usual procedures supplied by Applied Biosystems, Inc. Purification was typically accomplished by HPLC using a C-4 or C-18 column eluted with a gradient of acetonitrile/0.1M triethylammonium acetate.

The second probe, initially synthesized at a 19-mer oligomer (minus the 3' terminal base in the above sequence), was end labeled at the 3' terminus by the enzymatic addition of $N^4$-aminopropyl-dideoxycytidine-5'-triphosphate. The following is a typical synthesis of $N^4$-aminopropyl-dideoxycytidine-5'-triphosphate.

A bisulfite reaction mixture containing 1,3'-propanediamine (0.740 g, 10.0 mmol) in water adjusted to pH 7.08-7.12 by the addition of solid sodium metabisulfite (ca. 2.35 g are required) and the final volume adjusted to 10 ml was prepared. 2',3'-deoxycytidine-5'-triphosphate (100 mg) was added to 10 ml of the bisulfite reaction solution and the mixture was incubated at 37° C. for 60 hours in a tightly sealed vessel. The pH of the reaction solution was maintained at pH 7.1 by addition of small amounts of sodium metabisulfite. The progress of the reaction was monitored by high pressure liquid chromatography (HPLC). To isolate the product, the reaction mixture was diluted to a volume of 2.75 liters with deionized water and applied to a column of DEAE Sephadex A-25 (2.6×68/60 cm). Elution with a linear gradient of triethylammonium bicarbonate buffer (pH 7.8, 0.05-0.6M) and subsequent lyophilization of the appropriate fractions yielded $N^4$-(3-aminopropyl)-2'3'-dideoxycytidine-5-triphosphate. The solid was homogeneous by HPLC (RT=20.02 min., RT(ddCTP)=21.08) and characterized by UV lambda max. ($H_2O$=272.5 nm).

The amine labeled 20-mer probe was prepared by first synthesizing a 19-mer oligomer that was completed by addition of the $N^4$-aminopropyl-dideoxycytidine-5'-triphosphate (APddCTP) using terminal deoxynucleotidyl transferase (TdT). Typically, 0.85 O.D. units of 19-mer probe was first dissolved in 204 µl of sterile water. 5.0 µl of 10 mM APddCTP was then added, followed by 48 µl of 1M potassium cacodylate, 40 µl of 10 mM $CoCl_2$, 80 µl of 500µg/ml bovine serum albumin, and 16 µl of 15 mM dithiothreitol. The reaction mixture was warmed to 37° C. for 10 minutes and then to this was added 1050 units of TdT enzyme obtained from Supertechs (Bethesda, Md.). The enzymatic tailing reaction was allowed to proceed for two hours at 37° C. The enzyme was inactivated by heating at 65° C. for 10 minutes. The tailed probe (now a 20-mer) was then put onto a NAP-10 column (Pharmacia, Piscataway, N.J.) and eluted with water to remove all buffer components. The probe, which was recovered in approximately 1.25 ml of water, was then dried in a speed vacuum concentrator (Savant, Farmingdale, N.Y.).

Separation of the labeled coumarin probe from the unlabeled probe was performed on a Fast Protein Liquid Chromatograph (FPLC) from Pharmacia (Piscataway, N.J.). The coumarin probes were loaded onto a reverse phase (15µm) column and eluted with an acetonitrile gradient of 0.75%/min. at 2.0 ml/min. Since both the acetonitrile and the other component of the FPLC buffer system (TEA-acetate pH=7.0) were volatile, the recovered probes were dried with no residue remaining. Typically, 50 to 70% of the injected probe was recovered.

Preparation of 3'-Radioactive Tailed Coumarin Probes

Radioactive 10-mer probe was prepared by the enzymatic addition of dideoxyadenasine-5'-triphosphate-[$\alpha^{32}P$] (ddATP-[$\alpha^{32}P$]) to the 3'-end of the 9-mer coumarin-labeled probe. A typical reaction consisted of dissolving less than one unit of probe in 175 µl of sterile water. 250 µCi. of ddATP-[$^{32}P$], obtained from Amersham (Arlington Heights, Ill.) was then added followed by 48 µl of 1M potassium cacodylic acid (pH =7), 40 µl of 10 mM $CoCl_2$, 80 µl of 500 µg/ml bovine serum albumin, and 16 µl of 15 mM dithiothreitol. After warming to 37° C. for 10 minutes, 300 units of TdT was added. The tailing reaction mixture was incubated at 37° C. for 2 hours and then stopped by heating to 65° for 10 minutes. The probe was then purified by applying the reaction mixture to a NAP-10 column and eluting with water. The resultant radioactive 10-mer was then dried in the speed vacuum concentrator and stored at −20° C. The tritium labeled probes were prepared by the same procedure sustituting ATP-[$^3H$], obtained from New England Nuclear (Boston, Mass.) for the ddATP-[$^{32}P$].

Preparation Of 5' Radioactive DNA 30-mer target DNA and 20-mer probes were radioactively labeled on the 5' end by the same kinase reaction. Approximately 0.25 units of DNA were dissolved in 5 µl of sterile water. To this was added 4 µl of 5× forward reaction buffer (0.25M tris:HCl (pH 7:6), 50 mM $MgCl_2$, 25 mM dithiothreitol, 1 mM EDTA), 6 µl ATP-[$\gamma^{-32}P$], obtained from New England Nuclear, and 5 µl (50 units) $T_4$ kinase. The reaction was incubated at 37° C. After three hours the reaction was stopped by adding 80 µl of 1× SDS buffer (0.5% sodium dodecylsulfate, 5NM EDTA, 0.1M NaCl, 10 mM TRIS, pH 7.4) The reaction mixture was then extracted twice with phenol/chloroform and once with chloroform. The aqueous portion was the purified over a prepacked G-25 column (5' to 3' Inc., Paoli, Pa.).

The first and second probes all having reactive amine functional groups were reacted with N-hydroxysuccinimide esters of the coumarin derivatives. The following protocol is typical. In a standard conical plastic tube, about 10 nmole DNA were combined with an excess of 1200 nmoles of the N-hydroxysuccinimide ester coumarin derivative in 0.1M 3-(N-morpholino) propanesulfonic acid (MOPS) buffer (pH 7.2) at 37° C. The reaction mixture was allowed to incubate for 16-36 hours.

EXAMPLE 3

Hybridization and Laser Irradiation

In a typical photoligation procedure, the probe and target DNA were dissolved in 100 mM NaCl, 10 mM $NaH_2PO_4$ buffer, pH=7.2. Solutions containing probes and target were diluted using the same buffer. The ligation solution consisted of both coumarin-labeled probes and the 30-mer target. Before irradiation the solution was heated to 65° C. for five minutes in a water bath, to denature the probes and target, and then allowed to cool to room temperature over a 45 minute to 1 hour period. The solution was then transferred to a water bath at 5° C. where it remained for 10 minutes.

A 100 µl portion of the solution containing hybridized probes and target was then transferred to a semimicro cuvette masked on two sides with a path length of 1.0 cm (Helma Cells Inc., Jamaica, N.Y.). The cuvette was secured in a thermojacketed cell holder aligned in the beam path of the exciting source, and prequilibrated to 5° C. The cell holder was located within a sample compartment which was purged with nitrogen to prevent condensation of moisture on the cuvette walls. The excitation sources used for ligation were either a continuouis beam Helium-Cadmium laser (Liconix, Sunnyvale, Calif.) or a pulsed beam Nitrogen laser (EG&G Model 2100, Princeton, N.J.). The power of the He-Cd laser incident on the cell was 7.0 mW and the incident energy of the $N_2$ laser was 0.2 mJ/pulse. The pulse rate for the Nitrogen laser was set at 10 Hz.

Also, irradiations have been performed using a 200 W Mercury arc lamp (Ushio Model OSH-ZOODP, Japan) filtered with two Corning No. 0-54 Filters to remove light below 300 nm.

The dissolved oxygen in each sample was removed prior to irradiation by supplying an argon gas flow at 0.2 standard cubic feet per hour into the cuvette. Degassing was conducted for 6 minutes prior to irradiation as well as during irradiation. Irradiation periods lasted from 1 to 1000 seconds on the Helium-Cadmium laser or from 14 to 14,000 pulses when using the Nitrogen laser at 10 Hz pulse rate.

A portion of the irradiated sample was placed in the speed vacuum concentrator and dried. The dried sample was then redissolved in a 80:20 formamide:water solution and loaded onto a 2.0% polyacrylamide, 5% bisacrylamide, 7M urea denaturing gel. The samples were subject to electrophoresis for 1.5 hours at 50° C. and 500 volts. X-ray film was then placed against the gel and exposed for one hour before developing. The film was then carefully placed back against the gel in the original position and the regions of the gel containing radioactivity excised. In order to remove the DNA from the gel prior to measurement of the radioactivity the gel slices were mixed with 2 ml of 0.1M TRIS, 0.1M boric acid, 0.2 mM EDTA buffer at pH 7.2, and cut into small pieces. The gel pieces were then allowed to extract overnight. The mixture was filtered the next day through a 0.45μ acrodisc (Gelman, Ann Arbor, Mich.) and the filtrate added to 10 ml of Scintiverse II Scintillation cocktail (Fisher, Fairlaum, N.J.). This was then counted on a Beckman LS8100 scintillation counter. Following 1 second of irradiation only the $^{32}P$ 10-mer could be detected on the gel, but on continuation of the experiment to 10,100 and 1000 seconds two new radioactive bands appeared, the major of which, by comparison with molecular weight standards, is approximately a 30-mer and the minor approximately a 40-mer.

These data suggest that the 30-mer was formed by photoligation of the two probes and the 40-mer was formed, as a side reaction, by photo-crosslinking of the 10-mer to the 30-mer target. The yield of photoligate (obtained by excising the DNA bands from the autoradiogram and scintillation counting) was around 30% based on conversion of $^{32}P$-10-mer.

In the absence of target, none of the 30-mer species could be detected by polyacrylamide gel electrophorosis (PAGE), providing evidence of a template directed photoligation. Similarly, a probe photoreaction product could not be detected when a 30-mer sequence containing a 40% mismatch of base pairs relative to both 10-mer and 20-mer probes was substituted for the complimentary target. Similarly, a probe photoreaction product could not be detected when $^{32}P$ 10-mer and target, but no 20-mer was present. Similarly, a probe photoreaction product could not be detected when $^{32}P$ 10-mer, target and non-coumarin labeled 20-mer was present, i.e., one of the coumarins was missing. And, a probe photoreaction product could not be detected when neither 10-mer or 20-mer were coumarin labeled (10-mer was $^{32}P$ labeled) and target was present.

When the target 30-mer was labeled with $^{32}P$, and both 10-mer and 20-mer contained coumarin, the 30-mer probe photoreaction product could not be detected by autoradiography (but was present). These data suggest that the target was not involved in the formation of the 30-mer photoligate band.

In a further procedure, the second 20-mer probe was labeled with $^{32}P$ instead of the first 10-mer probe. Following hybridization to the target, photoactivation of the coumarin derivatives and PAGE separation of the constituents of the sample, the probe photoreactant band was excised and monitored. The probe 30-mer photoreaction product band appeared as usual.

In a still further procedure, the first 10-mer probe was labeled with $^{32}P$ and the second 20-mer probe was labeled with $^3H$. Following hybridization to the target, photoactivation of the coumarin derivatives, and PAGE separation of the constituents of the sample, the probe photoreactant band of the gel was excised and monitored. Multi-channel scintillation counting indicated that both radioisotopes were incorporated into the 30-mer band.

In a further procedure, the photoreactant band was excised from the gel and subjected to Maxim and Gilbert sequencing techniques. Sequencing confirmed the presence of the 10-mer and 20-mer probes in the order anticipated for a probe reaction product.

Embodiments of the present invention are well suited for amplification techniques in which more than one signal per target molecule is generated. Thus, a single target molecule may be the template for additional first and second probes forming multiple probe reaction products after photoactivation. Thus, by denaturation, and renaturation and photoactivation cycles, more than one probe reaction product may be generated from a single target molecule.

In a further procedure, a tenfold excess of probe to target DNA was employed and denaturation and renaturation cycles were employed between two irradiation periods. The denaturation was believed to be necessary in order to dissociate the product of the first photoligation from the target DNA in order to allow a new pair of probes to hybridize with the target. The new probes were then to be photoligated during the second irradiation period. By this procedure, a maximum of two ligated probes would be produced after irradiation following the first denaturation renaturation cycle. Since approximately 30% ligation efficiency was observed in previous experiments, 0.6 ligations per target were expected after two irradiation periods. Surprisingly and unexpectedly, analysis of the photo products show that three probe ligations have been achieved per target molecule. Even more surprising was the fact that the same amount of photoligation had occurred in a control experiment in which the denaturation renaturation step was omitted entirely. No photoligation was observed in the absence of target DNA and a single 23 minute irradiation was found to be sufficient for the maximum effect.

Apparently, the probe reaction product dehybridizes or is displaced from the target DNA by the excess probe or by local thermal effects or by steric effects without the need for physically changing the gross sample conditions. Data for amplification experiments, using 7-methoxy-coumarin-6-oxybutyric acid N-hydroxysuccinimide ester, is presented below in Table 1.

TABLE I

| Reactants | | Photoproducts | | [target- |
|---|---|---|---|---|
| [probes] (each) | [target] | [10 mer–20 mer] | [10 mer–20 mer] [target] | 10 mer] [target] |
| 1 μM | 1 μM | 0.48 μM | 0.48 | 0.11 |
| 1 μM | 0.1 μM | 0.32 μM | 3.2 | 0.69 |
| 1 μM | 0.01 μM | 0.26 μM | 26 | 4.9 |
| 1 μM | 1 nM | 37 nM | 37 | 6.5 |
| 1 μM | 0 | 3.6 nM | — | — |
| 10 μM | 0 | 0.37 μM | — | — |

Using one micromolar probe, samples containing 10 and 1 nanomol target provided ligated probes at levels approximately 30 fold greater than the level of target DNA present in the samples. One factor which may limit the amount of amplification appears to be the amount of side reactions which cross-link the probe to target DNA thereby destroying the catalytic properties of the target. At 0.1 micromolar target, the target is nearly completely consumed by the end of the experiment. In the 10 and 1 nanomolar target assays more cross-link target was found than possible. The amount of radioactivity collected from polyacrylamide gels is low for these samples and their values are therefore sensitive to contaminations from the high levels of radioactivity in other regions of the gel.

Selecting photoreactive functional groups may limit the undesirable cross-linking reaction. Various coumarin derivatives were applied to photoreaction protocols to determine the number of cross-linked and probe reaction products. The results are summarized in Table II for coumarin 7-oxybutyric acid N-hydroxysuccinimide ester, coumarin-5-oxybutyric acid N-hydroxysuccinimide esters, 4-methylcoumarin-7-oxybutyric acid N-hydroxysuccinimide ester, 7-methoxycoumarin-6-oxybutyric acid N-hydroxysuccinimide ester, and coumarin-6-isothiocyanate labeled probes.

TABLE II

| | Equimolar Probes and Target (1 μM) | | 10-Fold Excess Probes (1 μM Probes) | |
|---|---|---|---|---|
| Coumarin Derivative | % Ligated | % 10-mer crosslinked | % Ligated | % 10-mer crosslinked |
| coumarin-7-oxybutyric acid* | 24, (61***) | 5.6, (19***) | 22, (12***) | 5.2, (3.5***) |
| 4-methylcoumarin 7-oxybutyric acid* | 12 | 6.3 | 6.3 | 3.6 |
| Coumarin 5-oxybutyric acid* | 78 | 0.97 | 14.6 | — |
| Coumarin-6-isothiocyanate | 15 | 5.1 | — | — |
| 6-methoxycoumarin-7-oxybutyric acid* | 21 | 2.0 | 6.1 | 0.91 |
| 7-methoxycoumarin-6-oxybutyric acid* | 10, (17**) | 1.7, (1.3**) | 2.3 | 0.37 |

(—indicates no reading)
*N-hydroxysuccinimide ester.
**Data obtained by doubling the irradiation from 2.8 J to 5.6 J.
***Represents preliminary data, later data has consistently shown higher crosslinking values.

These data suggest that the composition coumarin-5-oxybutyric acid N-hydroxysuccinimide ester produces little cross-linked side reaction products of probe to target and may be advantageous in producing additional probe reaction products from a single target molecule.

Embodiments of the present application feature amplification methods wherein more than one probe reaction product molecules are created from a single target template. Preferred embodiments allow amplification without physically changing gross sample conditions, for example raising and lowering temperature, altering pH, altering salt strength, which would greatly increase the amount of time required for producing larger quantities of signal.

Embodiments of the present invention are well suited for clinical applications wherein an assay must be completed within a limited time frame. Thus, while preferred embodiments of the present invention have been described, the present invention is capable of variation and modification and, therefore, the invention should not be limited to the precise detail set forth, but should include such changes and alterations that fall within the purview of the following claims.

We claim:

1. A method for ligating polynucleotide ligands which are capable of binding to substantially contiguous portions of a target molecule comprising the steps of:

(a) contacting the target with a first polynucleotide ligand and a second polynucleotide ligand wherein said first polynucleotide ligand includes a photoreactive functional group and said second polynucleotide ligand includes a photoreactive functional group wherein said photoreactive functional groups are capable of interacting to form a covalent bond between said first and second polynucleotide ligands upon activation, and said first polynucleotide ligand and second polynucleotide ligand are capable of simultaneously binding to the target to form a target-first polynucleotide ligand-second polynucleotide ligand complex; and (b) activating the reactive functional groups to form a covalent bond between the first and second polynucleotide ligands while the first and second polynucleotide ligands are bound to the target.

2. The method of claim 1 wherein said photoreactive functional group has an extinction coefficient greater than 1,000 mole$^{-1} \cdot l \cdot cm^{-1}$ to permit excitation to reactive energy levels.

3. The method of claim 1 wherein said photoreactive functional group is selected from the group of photoreactive functional groups consisting of coumarins, psoralens, anthracenes, pyrenes, carotenes, tropones, chromones, quinones, maleic anhydride, alkyl maleimide, olefins, ketones, azides, polyolefins characterized by conjugated double bonds and ketone functionality and derivatives thereof.

4. The method of claim 3 wherein said photoreactive functional group is a coumarin derivative.

5. The method of claim 4 wherein said coumarin is characterized by the following features:

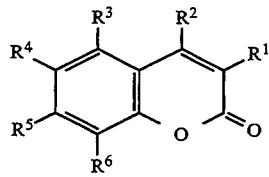

wherein, R groups 1 through 6 are selected from the group consisting of —H, —CH₃, —CH₂Cl, —CH₂Br, —CH₂I, —CH₂F, —CHCl₂, —CHBr₂, —CHI₂, —CHF₂, —CH₂OH, —CH₂OCH₃, —CH₂NH₂, —N₃, —COOH, —COOCH₃, —COOCH₂CH₃, —NH₂, —NO₂, —CBr₃, —CI₃, —CF₃, —CCl₃, —CH(CH₃)₂, —C(CH₃)₃, —Cl, —Br, —I, —F, and —O(CH₂)$_n$CH₃(n=0 to 10) wherein one of the R groups includes a functionality for linking to a polynucleotide.

6. The method of claim 3 wherein said psoralen is characterized by the following features:

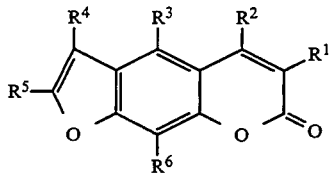

wherein, R groups 1 through 6 are selected from the group consisting of —H, —CH₃, —CH₂Cl, —CH₂Br, —CH₂I, —CH₂F, —CHCl₂, —CHBr₂, —CHI₂, —CHF₂, —CH₂OH, —CH₂OCH₃, —CH₂NH₂, —N₃, —COOH, —COOCH₃, —COOCH₂CH₃, —NH₂, —NO₂, —CBr₃, —CI₃, —CF₃, —CCl₃, —CH(CH₃)₂, —C(CH₃)₃, —Cl, —Br, —I, —F, and —O(CH₂)$_n$CH₃(n=0 to 10) wherein one of the R groups includes a functionality for linking to a polynucleotide.

7. A method for assaying a sample for target polynucleotide molecules comprising:
(a) contacting the sample under binding conditions with a first polynucleotide probe and a second polynucleotide probe, wherein the first polynucleotide probe includes a photoreactive functional group and the second polynucleotide probe includes a photoreactive functional group, wherein the photoreactive functional groups are capable of interacting to form a covalent bond between the first and second polynucleotide probes upon activation when the first polynucleotide probe and second polynucleotide probe are placed in a reactive position to form a polynucleotide probe reaction product, and wherein the first polynucleotide probe and the second polynucleotide probe are capable of binding to the target molecule to form a target molecule-first polynucleotide probe-second polynucleotide probe complex;
(b) subjecting the sample in the presence of the first polynucleotide probe and the second polynucleotide probe to radiant energy to form the polynucleotide probe reaction product; and
(c) monitoring the sample for the presence of the polynucleotide probe reaction product.

8. The method of claim 7 wherein said photoreactive functional groups undergo photochemical reaction upon excitation with photons having a wavelength of approximately between 300 nM and 380 nM inclusive.

9. The method of claim 7 wherein said photoreactive functional groups have an extinction coefficient greater than 1,000 mole$^{-1}$·l·cm$^{-1}$ to permit excitation to reactive energy levels.

10. The method of claim 7 wherein said photoreactive functional groups are selected from the group of photoreactive functional groups consisting of coumarins, psoralens, anthracenes, pyrenes, carotenes, tropones, chromones, quinones, maleic anhydride, alkyl maleimide, olefins, ketones, azides, polyolefins characterized by conjugated double bonds and ketone functionality and derivatives thereof.

11. The method of claim 10 wherein said photoreactive functional groups are coumarin derivatives or psoralen derivatives.

12. The method of claim 11 wherein said coumarin is characterized by the following features:

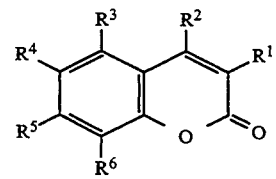

wherein, R groups 1 through 6 are selected from the group consisting of —H, —CH₃, —CH₂Cl, —CH₂Br, —CH₂I, —CH₂F, —CHCl₂, —CHBr₂, —CHI₂, —CHF₂, —CH₂OH, —CH₂OCH₃, —CH₂NH₂, —N₃, —COOH, —COOCH₃, —COOCH₂CH₃, —NH₂, —NO₂, —CBr₃, —CI₃, —CF₃, —CCl₃, —CH(CH₃)₂, —C(CH₃)₃, —Cl, —Br, —I, —F, and —O(CH₂)$_n$CH₃(n=0 to 10) wherein one of the R groups includes a functionality for linking to a polynucleotide.

13. The method of claim 11 wherein said psoralen is characterized by the following features:

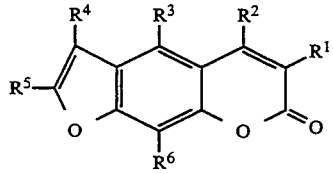

wherein R groups 1 through 6 are selected from the group consisting of —H, —CH₃, —CH₂Cl, —CH₂Br, —CH₂I, —CH₂F, —CHCl₂, —CHBr₂, —CHI₂, —CHF₂, —CH₂OH, —CH₂OCH₃, —CH₂NH₂, —N₃, —COOH, —COOCH₃, —COOCH₂CH₃, —NH₂, —NO₂, —CBr₃, —CI₃, —CF₃, —CCl₃, —CH(CH₃)₂, —C(CH₃)₃, —Cl, —Br, —I, —F, and —O(CH₂)$_n$CH₃(n=0 to 10) wherein one of the R groups includes a functionality for linking to a polynucleotide.

14. The method of claim 11 wherein said photoreactive functional groups are selected from the group consisting of coumarin-7-oxybutyric acid N-hydroxysuccinimide ester, 4-methylcoumarin-7-oxybutyric acid N-hydroxysuccinimide ester, 7-methoxycoumarin-6-oxybutyric acid N-hydroxysuccinimide ester, coumarin-5-oxybutyric acid N-hydroxysuccinimide ester, 6-methoxycoumarin-7-oxybutyric acid N-hydroxysuccinimide ester, and coumarin-6-isothiocyanate.

15. The method of claim 7 including the additional steps of removing said polynucleotide probe reaction product from said target, allowing additional first polynucleotide probe and second polynucleotide probe to assume a reactive position on said target wherein said additional first polynucleotide probe and second polynucleotide probe each include a photoreactive functional group, subjecting said additional first polynucleotide probe and second polynucleotide probe to radiant energy to form additional polynucleotide probe reaction product.

* * * * *